United States Patent [19]

Caines

[11] Patent Number: 5,021,064
[45] Date of Patent: Jun. 4, 1991

[54] ROBOTIC FLUID-ACTUATED MUSCLE ANALOGUE

[75] Inventor: R. Scott Caines, Greer, S.C.

[73] Assignee: Dolores R. Rudy, Midland, Mich. ; a part interest

[21] Appl. No.: 384,533

[22] Filed: Jun. 3, 1982

[51] Int. Cl.$^5$ .............................................. A61F 2/72
[52] U.S. Cl. ........................................................ 623/26
[58] Field of Search ................. 3/1, 1.1, 1.2; 128/1 R; 138/122, 123, 123, 124, 125, 126, 127, 128, 138, 153; 901/22, 23, 24, 25

[56] References Cited

U.S. PATENT DOCUMENTS

| | | |
|---|---|---|
| 489,193 | 1/1893 | Mills . |
| 2,373,455 | 4/1945 | Carey ................... 254/93 |
| 2,483,088 | 9/1949 | De Haven ................ 254/93 |
| 2,545,947 | 3/1951 | Felip et al. ................. 3/12 |
| 2,549,119 | 3/1951 | Wolfe ..................... 138/138 |
| 2,578,854 | 12/1951 | Stewart ................... 623/26 |
| 2,696,010 | 12/1954 | Robinson ................. 623/26 |
| 2,704,556 | 3/1955 | Blish ...................... 138/138 |
| 3,050,152 | 8/1962 | Blain ....................... 182/41 |
| 3,662,405 | 5/1972 | Bortz et al. .............. 623/16 |
| 3,830,519 | 8/1974 | Lewis ...................... 138/123 |
| 3,864,983 | 2/1975 | Jacobsen .................. 3/1.1 |
| 3,945,867 | 3/1976 | Heller Jr. ............... 138/123 |
| 4,078,670 | 3/1978 | Francois et al. ........... 3/1.1 |
| 4,393,728 | 7/1983 | Larson et al. ............. 623/26 |

FOREIGN PATENT DOCUMENTS

| | | |
|---|---|---|
| 0062139 | 6/1968 | Fed. Rep. of Germany ........ 623/26 |
| 62139 | 6/1968 | Fed. Rep. of Germany ........ 623/26 |
| 2106516 | 9/1972 | Fed. Rep. of Germany . |
| 2433710 | 1/1975 | Fed. Rep. of Germany ........ 623/26 |

OTHER PUBLICATIONS

"Robot Arm Developed," *Robotics WOrld*, Nov. 1984, p. 16.
Brown, S. F., "Rubber-Armed Robot," *Popular Science*, 226(5), May 1985, p. 28.
Hawley (Ed.), "The Condensed Chemical Dictionary, 10th Edition," Van Nostrand Reinhold Co., N.Y., 1981, p. 140.

*Primary Examiner*—David J. Isabella
*Attorney, Agent, or Firm*—N. Jerome Rudy; Christopher John Rudy

[57] ABSTRACT

An improved robotic contractile device having, besides general industrial and other-wages applicability for automation and other purposes, particularly attractive utility in and for prosthetic appliances and which is characterizable in being able to function in a way remarkably analogous to that of biological muscle is structurally made up of an expandable conduit which is contractible on fluid inflation with a plurality of longitudinally-directed filaments peripherally-secured thereabout that are connectable with an object to be moved or displaced as a result of the contractability experienced upon inflation of said conduit; there being associated means in the device for introducing and exhausting fluid under pressure to the interior of the said conduit in order to inflate same to effectuate its motive contraction action and deflate it to its normal rest condition of maximum or intermediate extension. The way of using the device takes advantage of the cooperative interaction of its constructional components and means.

76 Claims, 5 Drawing Sheets

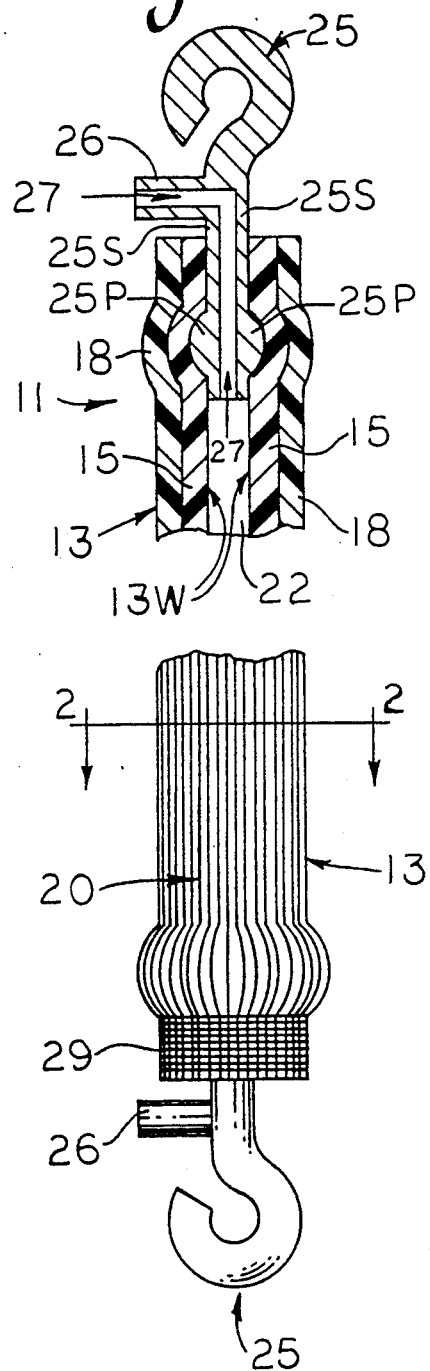
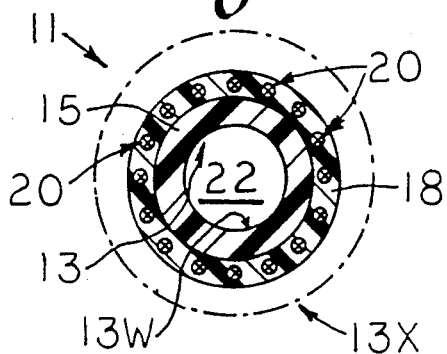
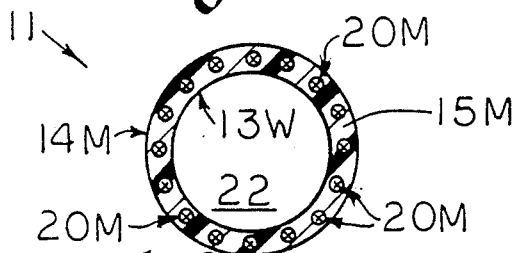
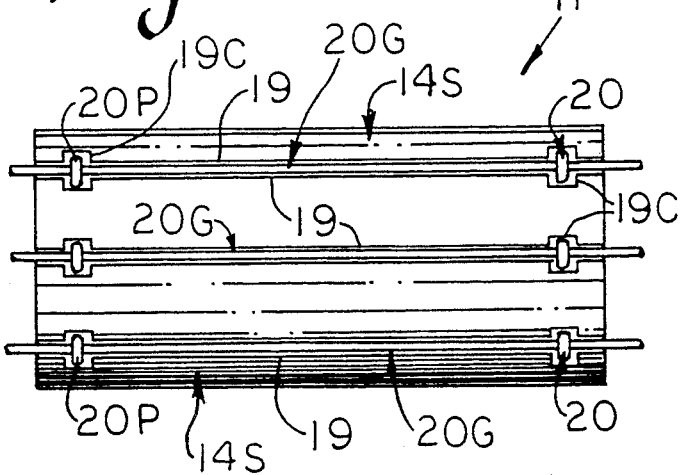

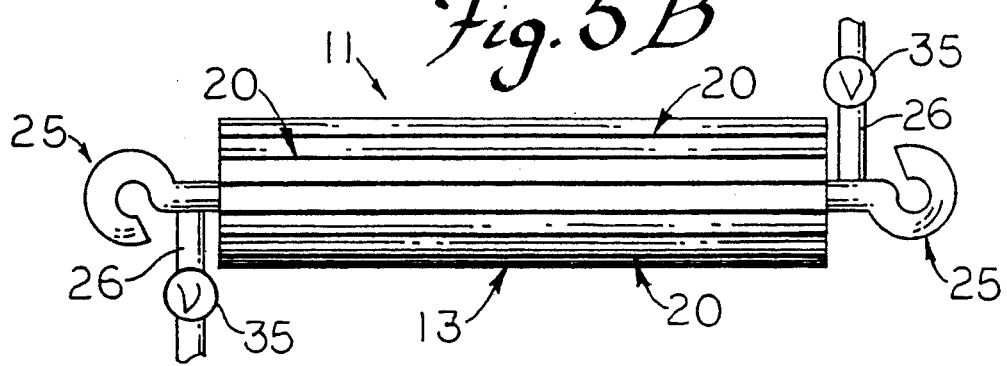
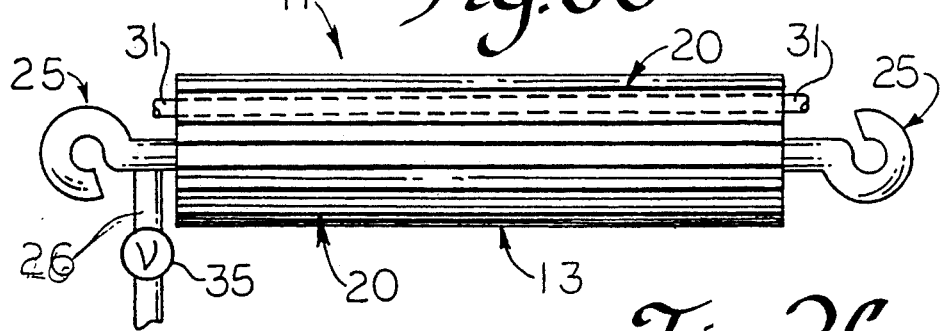
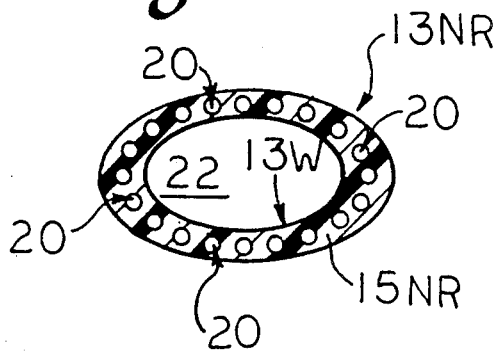
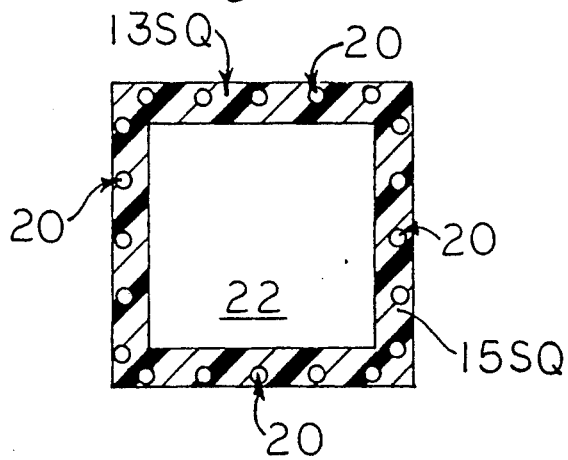

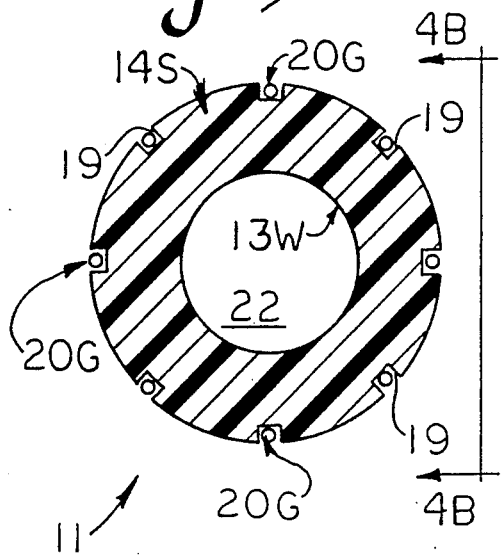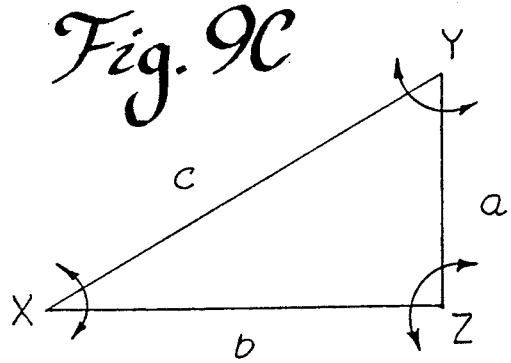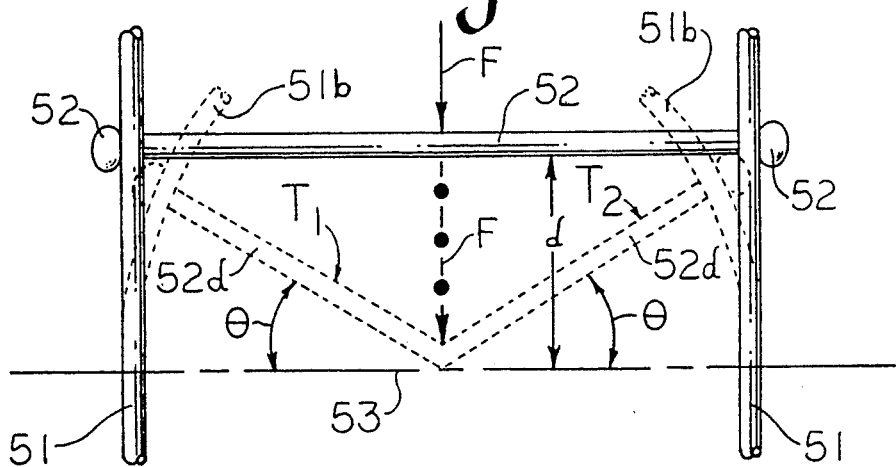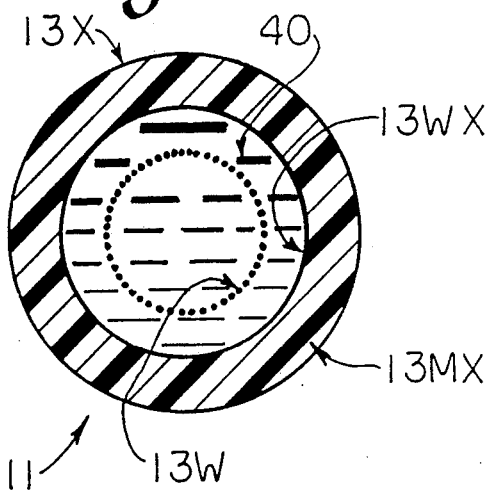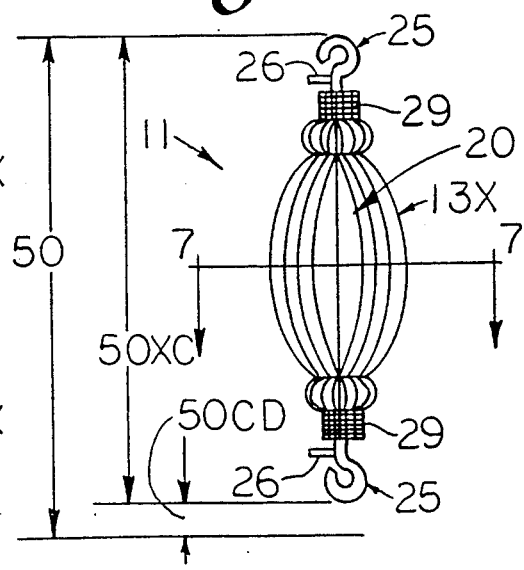

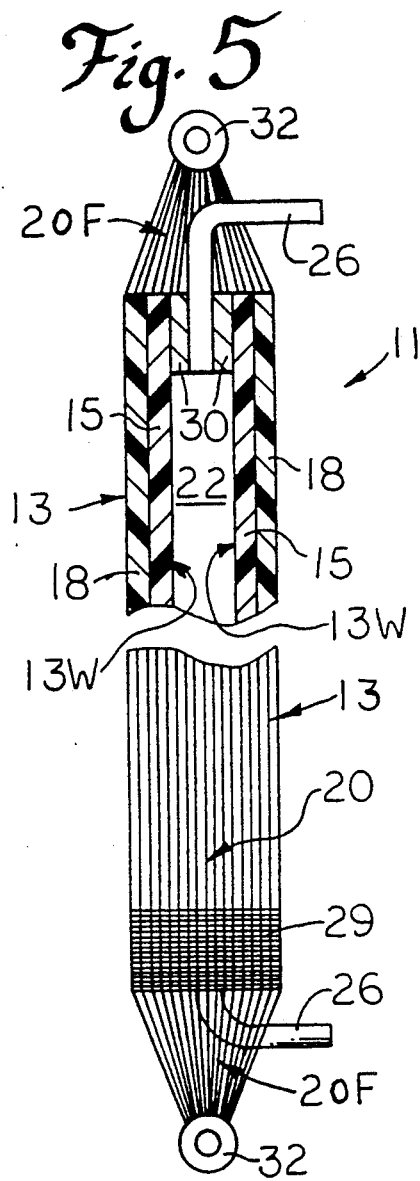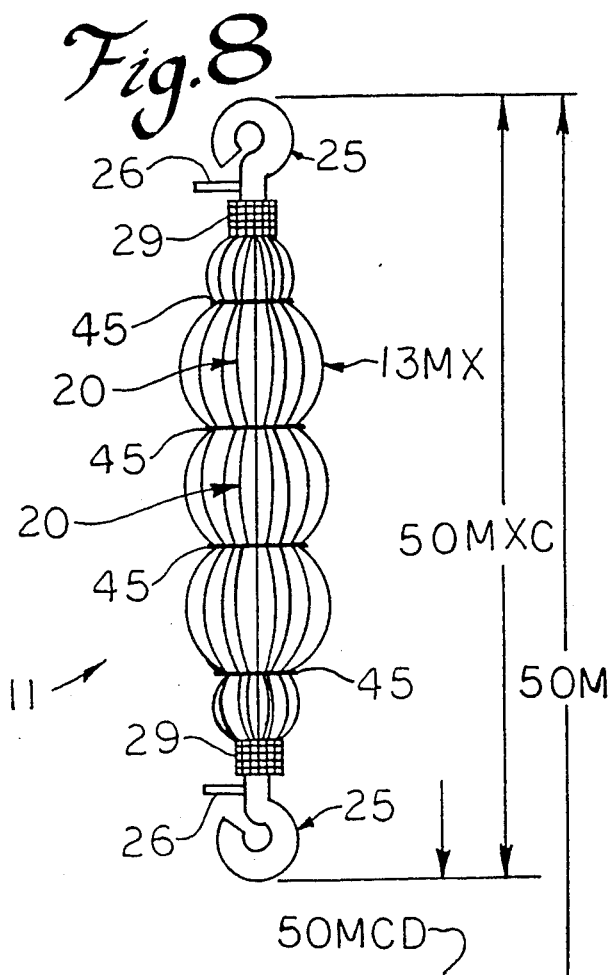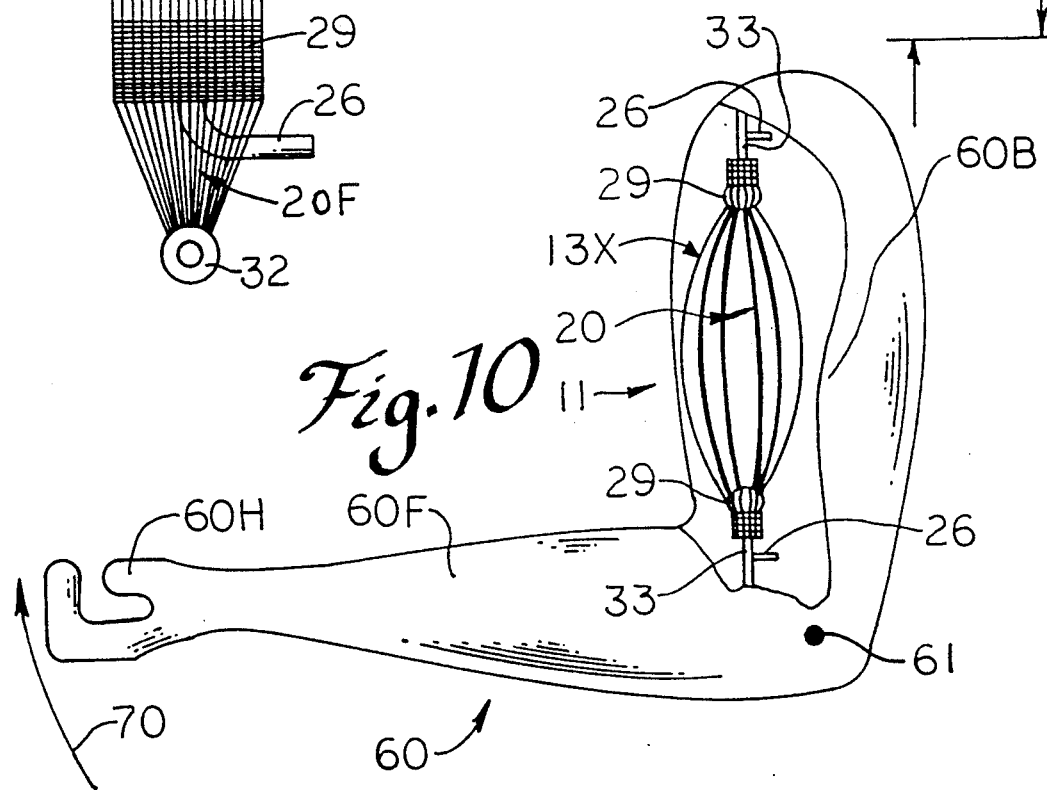

ROBOTIC FLUID-ACTUATED MUSCLE ANALOGUE

BACKGROUND OF THE INVENTION

As is well known, biological muscle is an organ having the special function of motion-production, as well as the tissue of which such an organ is comprised. A biological muscle consists of modified, usually greatly-elongated, cells (called muscle fibers) which contract when stimulated. The so-called striated muscles, which in vertebrates constitute the principal part of the flesh, are in typical cases made up of fibers bound together into bundles and enclosed in a sheath of connective tissue (known as the perimysium) which is continuous with the tendons, or fasciae. Each fiber is enclosed in a delicate membrane (i.e., the sarcolemma), which exhibits alternate transverse layers or segments of lighter and darker material (whence the name) and contains many protoplasmic nuclei (known as muscle corpuscles). In higher vertetrates (including homo sapiens), all those muscles that are at least partly under control of the will are striated. Hence, striated muscles are commonly called voluntary muscles, while those that are nonstriated are called, conversely, involuntary muscles. Non-straited muscles constitute a large part of the walls of the alimentary canal, blood vessels, uterus and bladder; also being found in the iris, skin and so forth. These are constituted of greatly-elongated, spindle-shaped cells with a central nucleus. The cells are usually grouped in bundles or sheets. Cardiac muscle, forming the substance of the heart of vertebrates and notable for its rhythmic contractions, is straited with its cells or fibers being extensively branched. In invertebrates, the muscle fibers exhibit varying degrees of differentiation and are, excepting in the Arthropoda, commonly unstriated.

As is also well known, the great preponderance of heretofore known robotic contrivances (including artificial limbs and other prosthetic contraptions) that have been developed to perform functions intended to simulate or be, perforce, substituted for the human or animal musculoskeletal system have, with almost overwhelming typicality thereabout, been literally completely-mechanical in nature. This is, in other words, to say that they have largely consisted of various assemblages of cables, pulleys, hydraulic and/or pneumatic cylinder and the like power drives and miscellaneous other items of hardware and implementation. It is not an unfair evaluation to characterize these previously-contrived mechanical creations as being, at best, relatively crude and primitive and not truly comparable attempts to simulate or even-reasonably-remotely replicate biological muscle.

Specifically representative and indicative of the sort of art that so far has been developed and is involved in the presently-contemplated field is that included in such items as: (A) U.S. Pat. No.: 439,193 which discloses a hoist comprising a hollow flexible tube that is wrapped in a sinuous fashion around several fixed spools in such a way that when a pressurized fluid is introduced into the tube it expands so as to cause such a shortening of and in its length as to suffice it for the lifting of a weight; (B) U.S. Pat. No.: 2,373,455 concerning a particularized style of hydraulically-implemented hoist, etc.; (c) U.S. Pat. No.: 2,483,088 which shows a knitted or woven tube used to reduce the shock of landing in a parachute wherein a small explosive charge produces the expansion of the tube; (D) U.S. Pat. No.: 2,545,947 involving a pneumatically-inflatable and -actuatable artificial hand; (E) U.S. Pat. No.: 3,050,152 pertaining to another sort of portable hoist including in its activating construction an inflatable, coiled flexible member which motivates the assembly when it is blown out to an uncoiled disposition; and (F) German Offenlegungsschrift (i.e., "OLS") No.: 2,106,516 which demonstrates a flexible lifting apparatus that functions by introducing a liquid or gaseous fluid, such as water or air, into the hollow center of an elastic tube which may be and preferably is encased in fabric causing the tube to balloon and thereby become sufficiently foreshortened to produce a lifting effect or operation.

Thus and notwithstanding, nothing that, even remotely, is overwhelmingly evident in prior art seems nor appears to realistically concern itself with the provision and/or ways and means for meeting the definite and recognizable need of making available a reliable and dependable system of providing a system for prosthetics and other robotic uses of providing truly skeletal-like movement and actuating capability that is amazingly analogous to and like biological muscle not only in contractibility and the like features but also in size, shape, weight, texture and so forth by any implementation as in the way so crucially indigenous as is in the present contribution to the art.

FIELD AND PURVIEW OF THE INVENTION

The present invention, and the principle aims and objectives attainable in its practice, pertain(s) and direct(s) to a novel and, in the overall, unprecedented and exceptionally efficient means and technique and system of machinery and/or procedure which, for desired robotic, prosthetic and the like or equivalent applications, is remarkably analogous to and functionally- and performance-wise -equivalent to natural biological musculoskeletal arrangements in that it involves:

(i). an expandable conduit portion that is contractile in nature with longitudinal, at least substantially parallel filamentary or fibrous components therewith associated and integrally-attached much in the way of natural muscle; with the assembly being (ii). nicely adapted to be fabricated out of resiliently-imbued, relatively soft and supple materials of construction which can be made into working products as are characterizable in having at least nearly identical size, shape and weight features as does natural biological muscle; with the said assembly also exhibiting in operation (iii). bulging upon contraction quite similar to what is observable in actuation of biological muscle; in which contraction (iv). the actual distance or span involved in the contractile movement is relatively short and not of particularly pronounced length-reduction but capable in so being moved of generating considerable force upon its contractability that, similar to effects noticeable in biological muscle actuation, provide very powerful motivational influence(s); the same being realizable with (v). only moderate pressure requirements for the fluid utilized operation of the involved system; with (vi). the extensions-involved in working of the system in the longitudianlly-disposed fiber components being quite analogous to biological tendons in that they are employed to connect the contractile device of the invention to the skeletal structure being activated and put into working energization; there also being comparability with natural muscle arrangements in that (vii). the conduits and/or tubing accessories for fluid handling in the present artificial muscle analogue devices are, as it were, comparable in a sense to the veins and arteries contained in natural muscle structures; and, by way of further comparability with natural muscle arrangements, the feature that (viii).the fluid flow control into and out of the expandable conduit portion of the presently-involved artificial muscle analogue devices is advantageously effectuated by electromechanical valves or the like actuatable by electronic signals which are transmitted along wire or the like conductors thus being, also in a realistic sense, comparable to nerve members in and responsible for motivation of natural muscle arrangements.

The achievement and provision of all the advantageous results and desiderations indicated, with even more and additionally other benefits and remarkable realizations derivable in and from practice of the present invention, appear(s) and become(s) more evident in the ensuing description and Specification.

MATERIALS FOR USE IN PRACTICE OF THE INVENTION AND ITS MAKINGS

(I). The Expandable Conduit

The expandable conduit utilized in devices according to the invention is made of a flexible, generally elastic material of construction adapting it to be inflated by fluid interjected therein under pressure then, upon release or removal of the inflating pressure, to return at least substantially if not completely to its original, unpressurized form and shape. As is evident by its characterizing description, the expandable conduit is a hollow body or member. Quite often, the expandable conduit is satisfactorily provided when it has a more-or-less cylindrically tubular shape and cross-section. However, the conduit need not be circular in cross-section; it being possible and sometimes even preferable for it to be made so as to assume many other particularized configurations. Thus, its cross-section may be oval or elliptical or of some other, even irregular, curvilinear form; or it may be rectangular, square or otherwise polygonal in cross-sectional outline. Similarly, taking into account longitudially-extending configurations and possible patterns thereof, the conduit may also be made to conform to differing designs. Commonly, it has a regular tubular or the like or equivalent structure when in an uninflated condition. However, it can oftentimes be of distinct advantage for the conduit to have variations in end-to-end cross-sectional features and outlines and, in some cases, to even have non-uniform resistance to expandability along its length in order to vary the contractile characteristics of the conduit member. Thus and for the indicated purpose, it may have thick-and-thin and/or regionally-reinforced wall sections and/or segments so as to facilitate a non-uniform expandability trait throughout the length and/or on certain portions of its body formation; or it may be segmentally-constricted along its lengthwise extension in order to purposively alter its characteristics and specific behavior of contractaility during expansion under pressurization (such encircling or otherwise encompassing constrictions, insofar as concerns practice of the present invention, not being any constructionally-associated part of or, derivation from the filamentary component placements—hereinafter more fully elucidated —laid and/or placed more-or-less peripherally-lengthwise with the extending direction of the conduit as occurs with and from woof threads, or even sometimes the warp, as results with usage of woven or other fabric or the like conduit encasements such as are employed per the teachings of the above-cited Reference {F}). In fact and as has been indicated, irregular configurations of the expandable conduit which may even include non-uniform part-by-part expandability characteristics thereof can be quite preferable for the design and utilization of same in devices pursuant to the present invention which are intended to be employed for various specialized purposes such as, by way of non-limiting illustration, in prosthetic applications wherein the implementation is wanted to function and perform in a manner as similar as possible to that of any given biological muscle that is therewith being replaced and/or supplemented. Thus and for further particularization of the physical constructional aspects of the expandable conduit(s) employed, the length, outside diameter (i.e., "O.D."), inside diameter (i.e., "I.D.") and other dimensions and specifications of and for same are to be chosen and designed according to what manner of architectural peculiarities may best fit and accommodate the anticipated application of the involved device, reckoning fully in this the performance capabilities wanted and/or needed for the intended usage. To somewhat amplify on this, there may be considered a given length or piece of an expandable conduit (such as, for example, a given diameter and wall-size unit of gum rubber tubing). When the tubing is subjected to internal fluid-pressurization, it will diametrically expand to the point where its resiliency is exceeded to the extent that further expansion would result in tube-rupture or -bursting, regardless of involved tubing length. Accordingly, when space limitations or other confinement restrictions prevail, the dimensions and other design characteristics of the involved expandable conduit are perforce made and selected so as to permit and facilite maximum and optimized contractibility and "muscle-power" efficacy.

(II). The Filamentary (Or Fiber) Components

The longitudinally-directed filaments that are combined with and/or in the expandable conduit member for assembly of devices that are in accordance with the present invention are capable of being taken from any one or more of a wide variety of natural, synthetic and artificial materials. Depending to appropriate extent on and of what they are composed, the filaments utilized may be of either monofilament or multifilament construction (including in the latter combined continuous-length monofilaments and those of either braided or twisted construction whether or not made from monofilaments or spun staple fiber lengths or combinations thereof). Of course, depending upon the size and power capacity of the involved device, the exact number, dimensions and other characteristics of the selected filamentary material (giving due regard to its inherent tensile strength, etc.) can be readily-enough determined. The particular manner of mechanical combination to be utilized for competent association of the filamentary materials with the expandable conduit member is also, as is evident on introspection, a factor in suitable selection(s) to be made.

As is easily comprehensible, the filamentary material employed must have adequate flexibility thereabout to facilitate its necessary bending cooperation with expansive movement or "ballooning" of the expandable conduit member upon internal pressurization thereof. In this, it cannot be so stiffly rod- or bristle-like in character as to possibly result in its militation against such requisite capability. Its extensibility should also be such as to ensure total elongation thereof under pulling tension upon operation of the device that is less, taken on a length- or distance-wise basis, than the distance of contraction experienced by the expandable conduit under any given condition or extent of fluid-pressurized expansion. Ideally, in this connection, a suitably-flexible filamentary or strandular material for utilization would have a "zero" extensibility.

Notwithstanding and as is also readily recognizable by those skilled in the art, even if there is—or when there may be—some elongation of the filaments involved in their integral association with and fixation to the expandable conduit member, the consequence is not of fundamentally significant or really deleterious import; this being especially the case in applications wherein the contractile device is intended to be analogous to biological muscle (as in humanoid-like robot assemblies). In such situations and as naturally occurs, the muscles are invariably always positioned in opposing pairs such that other associated and cooperative muscle displacements can pull back or retract the involved limb or other anatomical part (or vice versa in case of extensions or pushings out). This is well illustrated by the constitution and operation or working of the biceps and triceps muscles of the upper arm in a human body. Actually in and for such applications, it could oftentimes well be advantageous to have some lesser or greater pre-stretching of the longitudinally-extending filaments utilized in the contractile device assemblies of the present invention.

For practical purposes, however, the filamentary material employed need only have an adequately low percent elongation property under given tensile loading as to preclude material or ineffectual stretching of the strand during expansive-contraction of the conduit to such extent as would prevent the pulling tractile-effort force desired and needed to be exerted by the device upon the load being moved in filamentary coupling (of one sort or another) with the device during its operation. Obviously, the less extensibility in the filamentary material as compared to the contractive movement of the expandable conduit at any given condition of pressurization and tractive-pulling-power being exerted, the more efficient is the device at least with respect to stroke-length capability and ratio relative to contractile-movement distance of the expandable conduit upon pressurizing expansion thereof.

The exact length of the filamentary materials employed is not critical so long as it is in good correspondence with the length of the expandable conduit with which their association is made and suffices to allow ready attachment to whatever means or thing whether or not done with intermediate coupling connectors, etc., is to be subjected to the exerted force of contraction on operation of the device. The number of filaments employed in any given device depends in large measure on their individual strengths as compared to the total load contemplated to be necessary to move to avoid any possibility of filament breakage during operation as well as upon the given size of the device involved. Larger devices may require either greater numbers of incorporated filaments or stronger and sturdier individual filament constructions to be utilized. Thus, depending on such factors, the actual filaments employed may be (at least insofar as relatively empirical, at-least-nominal diameter sizings or grades are concerned, again giving due regard to the involved strength of the material from which any given filament is made) classified or characterized as being: mere filaments; threads, strings, yarns; lines; cords; ropes; and so forth as is descriptive of various cordages and the like strandular goods (even cables, etc.).

While, hypothetically, only a single filamentary length need be associated with the expandable conduit, it is generally the case that a plurality of at least two strandular lengths are utilized in the device. This, especially when peripheral equispacing is involved, tends to assure better and more uniform (with much reduced opportunity of failure thereabout) pulling tractile effort through and by means of the attached filamentary material upon the contracting expansion of the expandable conduit or other bladder-like component in the device. As a practical rule of thumb, the number of filaments utilized in devices made in accordance with the present invention frequently depends upon and is increasingly numerically variable with the circumference or other peripheral size of the expandable conduit that is employed. Thus and while it is not invariable, it is ordinarily-encountered that the larger the circumference or like or equivalent measurement of the conduit, the more longitudinally-attached filaments or fibers are required and/or employed. Of course, with any given circumferential size (or the like) of the conduit taken with given fiber diameters or denier or the like measurements, the maximum number of longitudinally mounted and -extending filaments that can be used depends on whether one or more layers (whether or not identically spaced from the axis of the conduit) are utilized; it being possible along this line to have more than a single layer or associated array of filaments encompassing the conduit in devices assembled pursuant to the invention (with this, again, being relatable to involved strengths of materials and designed contractile force or pulling capacity planned for the device amongst other factors of pertinence that are involved in such considerations). Nonetheless, placement of multiple fibers about the expandable conduit in devices that are in accordance with the present invention is most frequently of utmost advantage in order to have maximum benefit of the contractile force developed upon pressurized expansion of the conduit relative to increased or increasing diameter thereupon as well as to help contain the expanded or expanding conduit member.

Although workable deviations in specialized instances and for specialized purposes may on relatively-unusual occasions be followed, resort is usually preferably had in the/disposition of the fibers about the circumference or other periphery of the conduit to longitudinally-attach and -associate them there with uniform spacing of the fibers in such a way that they are laid and placed parallel to one another as well as to the axis or other general longitudinal direction of the expandable conduit. This, corresponding to the general preferability of using a plurality of filaments about the conduit rather than just a single fiber attachment, tends greatly to secure a more balanced and uniformly-distributed pulling effort through the installed fibers about the conduit on the contractile action of the latter when undergoing fluid pressurization. Along this line, it is also generally much preferred in most instances for the plurality of filaments employed to be all of the same size and material. Nonetheless, it is not impossible (again, in certain specialized instances and for certain specialized purposes) to intermix various sorts of filaments as to either their constitutional make-up(s) or physical sizing(s), or both, for attached association with a given conduit in and for a given device fabricated and used in accordance with the present invention.

There are many quite satisfactory ways to mechanically associate the longitudinally-extending filaments employed in good cooperative securement to and with the expandable conduit that is therewith outfitted. They can, for example (and oftentimes with great advantage), be incorporated directly in the expandable conduit during manufacture of the latter by embedment therein within the wall structure of the conduit in a manner much like that followed for the reinforcing of pneumatic tires with tire cord and/or of such mechanical rubber goods as hoses and beltings with intentional internally-provided filamentary and the like reinforcement components. In such cases, especially when the conduit is of a natural or synthetic rubber-type elastomer, materials equivalent or analogous to appropriate tire cord dips and/or applied and/or incorporated materials may be utilized with the filaments to enhance their mutual adherence and strong inter-bonding to and with the body of the conduit being so-furnished with the filamentary attachments. Another good way to make the physical association is to lay the fibers (one at a time or simultaneously just so long as the suitable desired relative positioning of the fibers is maintained) in one or more layer assemblages about the conduit while making the firm attachment with a suitable adhesive or glue such as, by way of illustration, a rubber coating from natural or synthetic rubber latex or equivalent preparation painted or otherwise applied about the placed filaments in their location on the outer (or even inner) wall surface of any natural or equivalent synthetic rubber conduit. In place of brushing, the latex or like or equivalent adhesive coating deposit may be applied by dipping or spraying techniques. Drying between the latex or the like applications is generally the best procedure to follow; and the quantity of applied adhesive may merely be enough to inter-bond the placed filaments with the conduit surface or, in many instances, of such larger proportion(s) as will envelope and/or encapsulate the filaments being affixed on and to the conduit in the applied coating of the adhesive. Natural rubber latex adhesive with natural rubber conduits generally provides and yields excellent combination for filament fastening purposes. Of course, elastomeric material other than natural rubber latex or its like or equivalent may be utilized (provided it has adequate adhesive and cementing affinity therefor) to secure the particular filaments being employed when given elastomeric material(s) other than natural or the like or equivalent synthetic rubber (such as a natural gum rubber tubing or other form structure) is employed for the conduit. A further good alternative for association of the longitudinally-extending filaments on and with the conduit is by strictly mechanical inter-joining and positioning. This may be accomplished by placing the filaments in accomodating grooves or other recesses in the wall of the conduit or even in longitudinal bores or the like apertures tunneled through and lengthwise of the conduit wall with suitable anchoring means attached to the filaments (such as knots, projecting attachments of washer-like or equivalent form, slugs and so forth) to hold the filaments in place with the conduit in accommodating lock recesses or the like or by other mechanical coupling expedients. Even stapling or equivalent mechanical fastening means may sometimes be used for the fastening (provided, of course, that no fluid-leaking puncture of the conduit wall is incurred in any such operation); and resort may also be had to even other mechanical binding techniques for strong and reliable affixation of the filament(s) on the conduit as will occur to those skilled in the art.

Regardless of fastening technique utilized for filament association, the important thing is that the attached filamentary material be so well secured on and-/or to and/or with the conduit that the fiber components involved maintain their intended position with respect to the conduit in their affixment therewith, particularly during and after completion of the inflating expansion action of the conduit during its contracting operation in working of the device in which it is involved (allowing in this, and of course, for any involved and inconsequential extensibility of the filamentary material when it is under load-moving, pulling tensile stress and strain). They need to have an excellent cling to or in the conduit.

The filamentary materials utilized may be any desired and satisfactory fiber product of organic or inorganic natural or synthetic (including artificial) origin. These, by way of non-limiting illustration, include:

1). As Organic Fibers Of Natural Origin
   1a). Such proteins and proteinaceous materials as hair, wool, silk, tendon and the like;
   1b). Such cellulosics as cotton, hemp, ramie, flax (i.e., linen), sisal, wood fiber and the like; and
   1c). Such other natural high polymer substances as alginates (i.e., algae), chitin and/or carbohydrates other than cellulose (xylan).

2). As An Inorganic Fiber Of Natural Origin
   2a). Asbestos.

3). As Organic Fibers Of Artificial (Synthetic) Origin
   3a). The various rayons or artificial silks, including viscose rayon, acetate (and other like derivative) rayon(s), cuprammonium rayon and so forth;
   3b). Polyamides, such as many of the various nylons;
   3c). Polyacrylic derivatives (usually from fiber-forming polymers and copolymers of acrylonitrile), such as "ORLON" (Reg. TM) which is commercially available from E.I. DUPONT deNEMOURS & CO., Inc. and the like;
   3d). Polyesters, such as "DACRON" (Reg. TM) which also may be gotten from the said DUPONT Company;
   3e). Polyvinyl derivatives, particularly those comprised of various of the fiber-forming polymers and copolymers of vinyl chloride and especially such vinyl chloride/vinyl acetate copolymeric materials a "VINYON" (Reg. TM) from Union Carbide Corporation an the like;
   3f). The fluorocarbon and chlorofluorocarbon group of fiber-forming polymers;
   3g). Filamentary materials from the sarans and other copolymers of vinylidene chloride;
   3h). Filamentary materials from polyolefins such as polyethylene, polypropylene, etc., and various aliphatic, monoethylenically-unsaturated olefin copolymers, plus halogenated (especially chlorinated), chloro-sulfonated and the like or equivalent forms thereof;
   3i). Fiber-forming silicone polymer products; and 3j). Various other fiber-forming, synthetic resinous materials, generally high-polymeric in nature.

4). As Inorganic Fibers Of Synthetic Origin

4a) Those from quartz, glass, aluminum and other silicates and the like or equivalent derivatives of silicon, including essentially ceramic products;

4b). Fibrous carbon and graphite substances and the like (including composite structures thereof);

4c). Boron and boron derivative materials;

4d). Those from iron and ferrous alloys, including many of the so-called "stainless" (or, more properly, corrosion-resisting) steels as well as galvanized and the like and other plated or coated ferrous products; as well as 4e). Those from many other metals and metallic alloys including such filamentary goods from or based on aluminum, copper, brass, bronze and so on and so forth.

Filamentary components of the nylons (including the "nylon 6—6", "nylon-6", from caprolactam, "nylon-7", etc., varieties), a great number of polyesters (such as the ethylene glycol terephthalate varieties) and their treated and/or specially formulated likes and equivalents are usually very good selections for many embodiments of devices capable of being made in accordance with the invention. Another excellent strandular material for utilization as the longitudinally-extending filament(s) and/or the like to be employed is "KEVLAR" (Reg. TM), a very tough and durable polyaramid product which is commercially available from said DUPONT Company that, besides having exceptionally great qualities of inertness, exhibits a very remarkably low extensibility and percentage of elongation characteristic under tension when fabricated into fiber form(s). Many of the polyurethane materials also provide fine filamentary products for use in present practice, quite irrespective of which desired form of funicular construction in which they are employed.

(III). Elastomer(ic) {i.e., "EL"} And Adhesive Materials

As has been mentioned various EL compositions are advantageously utilized for both constitution of the expandable conduit member utilized and the latex (or equivalent, including solvent-prepared or -fortified preparation) formulations employed for adhesively-securing or cementing the filamentary components to, with or about the conduit.

Particularly attractive for present purposes amongst the numerous EL's available for such usage(s) is natural rubber (otherwise known as Hevea Brasiliensis which generally consists of polyisoprene, also with correct nomenclature thereabout identifiable as poly-2-methyl-butadiene). This may, as indicated, be in the form of natural gum rubber for conduit fabrication or, also as indicated, as a latex or like or equivalent product for filament placement and connecting affixation thereof with the conduit.

Gum rubber as an EL for conduit-making in practice of the present invention is quite desirable since, besides being a material having good mechanical strength, it has remarkable elasticity and resilience thereabout. This permits considerable expansive stretching or ballooning of the conduit upon pressurized inflation thereof without substantial or deleterious physical deformation in order to return to its position and form of uninflated rest when there has been fluid pressure release (or removal) from a conduit in tubular or other bag- or bladder-like shape. Likewise, natural rubber latex or the like has excellent holding power for and with a great number of filamentary materials possible to employ and, as would be expectable, adheres well and very tenaciously to gum rubber structures, as well as to many other bodies of different EL's.

However, the EL utilized for both conduit fabrication and latex (or the like or equivalent) cementing formulations may also be selected from a wide variety of generally sulfur-vulcanizable or otherwise crosslinkable materials or mixtures thereof (including blends with natural rubber) which are representatively typified by polybutadiene synthetic rubber (i.e., "PBD"). In this connection, it is often advantageous for the solid EL employed to be, to some more-or-less extent, vulcanized or otherwise cross-linked in order to enhance the mechanical strength and rupture-resistance capability thereof. Of course, any such polymer molecule-interlinking treatment should not be so heavy or drastic as to disadvantageously interfere with or restrict satisfactory elasticity and consequent expandability potential of the conduit from a cross-linked EL material involved in the conduit fabrication. Along this line, it is also of benefit sometimes for the latex or the like or equivalent adhesive preparations to be made with somewhat (and usually not too heavily) cross-linked or crosslinkable EL ingredients.

Thus, besides natural rubber and as is the case with PBD, the EL employed can satisfactorily be a conjugated diolefine (homo)polymer synthetic rubber (or elastomeric inter- or co- polymer composition of between about 25 and about 90 weight percent, based on total composition weight {i.e., "wt. %"}) of a 1,3-diene of the Formula:

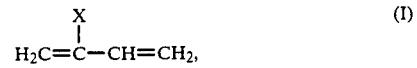

wherein X is selected from the Group consisting of hydrogen, chlorine and methyl radicals.

Such conjugated diolefine polymer synthetic rubber products are polymers, as is above indicated, of: various butadiene (i.e., "BD") monomers particularly butadiene-1,3 and other BD's-1,3; isoprene; 2,3-dimethyl-butadiene-1,3; and copolymers of mixtures of one or more such BD's (in a proportion of at least about 75wt. % of same) and, for example, of up to 25 wt % of the entire copolymerizable mass in such a mixture of one or more monoethylenic compounds which contain a:

grouping, wherein at least one of the connected R' and/or R" valences is attached to an electronegative group (i.e., a group which substantially increases the electrical dyssymmetry or polar character of the involved molecule).

A good and commonly-available and widely-used example of compound(s) which contain the Formula (II) grouping and are co-polymerizable with BD's are alkenyl aromatic monomers (which, often of greatest practicality and preference, are represented by styrene {i.e., "St."}) which are of the Formula:

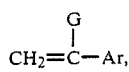     (III)

wherein G is selected from the Group consisting of hydrogen and methyl and Ar is an aromatic radical (including various alkyl- and halo-ring-substituted aromatic units) of from 6 to about 10 carbon atoms. These, besides St, frequently quite satisfactorily include such monomers as: α-methylstyrene(s); vinyl toluene; vinyl naphthalene; the dimethyl styrenes; t-butyl styrene; the several chloro-styrenes (such as the mono- and di-chloro variants); the several bromostyrenes (such as the mono- and di-bromo variants); isopropyl toluene; and so forth including various mixtures thereof.

Other ethylenically-unsaturated monomers includable in various EL co- and/or inter-polymerizates with the Formula (I) monomers are acid-containing structures of the Formula:

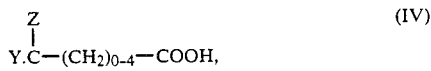     (IV)

wherein Z is selected from the Group consisting of hydrogen, alkyl radicals that contain not more than about 4 carbon atoms and carboxyl units when Y is devoid of any carboxylating attachments and Y is a monoethylenically-unsaturated substituent selected from the Group consisting of methylene, alkene and alkenyl units containing from 2 to about 5 carbon atoms (including vinyl, isopropenyl and other alkyl-substituted arrangements) and, when Z is not carboxyl, carboxylated methylene and mono-carboxylated alkenylunits containing from 2 to about 5 carbon atoms.

Representative of the carboxylating monomer constituents that are includable under the Formula (IV) are, generally, any of the acrylic acids (such as acrylic acid or "AA" and methacrylic acid or "MAA") as well as certain of the mono-ethylenically-unsaturated, dibasic carboxylic acids (such as fumaric and/or maleic acid{s}, itaconic acid, citraconic acid, mesaconic acid, isocrotonic acid) and so forth.

Actually, since they exert a rather profound adhesive-improving effect on EL compositions in which they are incorporated utilization of, say, ½-10 (preferably 1-5, or so) wt. % of a Formula (IV) monomer in a then so-called carboxylated latex (or like or equivalent cementing preparation) EL product is frequently a very desirable expedient to enhance filament-bonding strength and effectiveness. For comparable reasons, it is sometimes of advantage for certain situations to utilize a carboxylated EL as the material of construction for the expandable conduit to be utilized in a device that is in accordance with the present invention. And, in fact and with considerable relevance to this, many of the possible non-El polymers and copolymers to prepare from Formula (IV) monomers are, in and of themselves, excellent adhesive and cementing materials. These include, in particular, polymerizate products of AA and/or MAA and various derivatives thereof, such as the cyanoacrylate glues.

Consistent with the foregoing, yet other monoethylenically-unsaturated monomeric constituents that may be employed for preparation of EL interpolymerizates in that they are possessed of the Formula (II) grouping are other of the unsaturated carboxylic acids (including many possible to fit within the above-given Formula {IV} structuration) and their esters, nitriles, amide- and cyano-derivatives coming within the Formula:

     (V)

wherein $Q_1$ is selected from the Group consisting of hydrogen, lower alkyl units containing not more than about 4 carbon atoms and the monocyanogen radical and $Q_2$ is selected from the Group consisting of the hydroxyl radical, lower alkoxyl radicals containing not more than about 4 carbon atoms and amido units. Useful members of this chemical family above and beyond AA and MAA, which are also includable under said Formula (IV), are, inter alia, methyl acrylate, ethyl acrylate, methacrylamide and so forth.

A good number of very desirable EL materials useful for conduit formation include interpolymerized moieties alone with the Formula (I) diene monomers or in admixtures with other ethylenically-unsaturated addition monomers including those of the Formulae (II) and/or (III) and/or (IV) and/or (V) are the well-known cyano-alkylenes of the Formula:

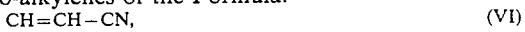
CH=CH—CN,     (VI)

wherein R is selected from the Group consisting of hydrogen and lower alkyl units containing not more than about 4 carbon atoms. Commonly-encountered Formula (V) monomers include acrylonitrile (i.e., "VCN" or "AN") and α-methacrylonitrile.

In fact, many of the so-called "ABS" or "ABS-type" resins, which are basically interpolymerizates of AN and St with PBD, are useful to employ as EL's in practice of the present invention. As is well known, a good number of the ABS materials and their analogous resinous products usually contain interpolymerized therein from about 20-35 wt. % AN and from about 80-65 wt. % St with between about 5 and about 18 wt % PBD (or equivalents thereof).

Yet other ethylenically-unsaturated addition monomers which may, and sometimes with great advantage, be reacted into the interpolymerizates forming EL products suitable for use in practice of the present invention include such materials, or mixtures thereof with one another and/or any one or more of the above-identified monomers besides those of the Formula (I), as: vinyl halides, particularly vinyl chloride; various vinyl organic acid esters such as vinyl acetate, vinyl propionate, etc.; vinylidene chloride; methyl vinyl ketone and methyl isopropenyl ketone; 2-vinylpyridine and 2-methyl-5-vinylpyridine; maleic anhydride; and so forth.

Besides polyisoprenes (including synthetic forms thereof) and PBD, other embodimentations of such conjugated diolefine polymer synthetic rubbers are: BD/St and the like or equivalent copolymers (i.e., "SBR", also called "GRS"); and BD/AN copolymers. The synthetic rubber may be solution-prepared or emulsion-prepared, be it a stereospecific variety or otherwise.

Other conventional unsaturated sulfur-vulcanizable rubbery EL's which also may be employed for conduit fabrication and/or latex or other adhesive formulation(s) used in practice of the present invention are: "EPDM" (a rubbery terpolymer of ethylene, propylene and a copolymerizable non-conjugated diene, such as 1,4-hexadiene, dicyclopentadiene, dicyclooctadiene, methylenenenorbornene, ethylidenenorbornene, tetrahydroindene, etc.); other ethylene/propylene and homologous olefin rubbers; polyurethane rubbers; chlorosulfonated polyethylene and the like polyolefins; and so forth. The analogous fluorocarbon, silicone and polysulfide rubbers may also see useful and desirable service as an EL in the practice and for the purposes of the present invention.

While, as has been indicated, it is undesirable to encase the expandable conduits made for use in practice of the present invention with fabric or equivalent relatively-total laterally-constrictive enclosures, it is possible to make such members from more than a single layer or ply of the particular EL employed for fabrication thereof instead using only a single thickness of same (regardless of how and/or by what casting, seaming, winding or other technique is employed for the production thereof) in the wall structure. In this connection, it is also possible to incorporate the filamentary materials within the wall structure of the conduit when it is made by certain multi-ply fabrication procedures. Also, if desired, combinations of different EL's in multi-ply wall structures for the conduits may also be utilized; such variations oftentimes possibilitating quite advantageous results including, for example, the ability to have a very strong ply for better expansion performance welded, joined or otherwise bonded with, say, an outer ply of more easily-adherable EL material in the composite structure; and so on and so forth with many conceivable adaptations of such sorts of combinations being desirable for given specialized and/or peculiarly-requiring applications and usages.

Coincident somewhat with the immediate foregoing and in amplification of the disclosure in the above Item (II) as to the possibilities for making essentially-mechanical fastenings of the longitudinally-extending filamentary materials or fiber components to, with or within and about or at least towards the exterior surface of the expandable conduit having such attachments thereto made, it is not impossible (and may frequently be of decided advantage) to also utilize an EL latex or like or equivalent adhesive to assist in and help pronounce the securement of mechanically-fastened filament(s). This, as is apparent, can bring about the filament-joining superiority of coalescing not only good mechanical fastening with (and adding thereto by) the added adhesional support of the supplementarily applied cementing- and bonding-agent. The same sort of double-featured filament securement can be readily done by applying the latex or other adhesive formulation over surface-exposed fiber placements that are primarily mechanically secured or, in the cases wherein the filaments extend through the length of the conduit wall(s) by passage traversing tunnel-bores and the like holes or apertures therefor (and wherein they are not continuously interjoined in tire cord fashion to the interior EL wall body structure) by forcing a filling adhesive into the annular space between filament and wall body or pre-supplying the adhesive to the filament surface before passing it through the accommodating longitudinal opening therefor in the body of the conduit wall structure (or, vice versa, by tunnel wall pre-coating).

(IV). Pressuring Fluids And Means

Regarded at least roughly or approximatively, the operation of devices pursuant to the present invention may (if only for epideictic purposes) be likened or considered akin to a thermo-dynamically adiabatic process. Thus, at any given steady-state condition or degree of inflation-extent of the expandable conduit under contractile load, it may at least relatively be considered to follow isentropic rules; while, during working inflation of the contractible expandable conduit, the laws of polytropic behavior may find logically associative rationale. Along this line, reasonable comparison of the presently-contemplated devices may also be made to the workings of a pistonless cylinder engine with non-rigid wall enclosure which yet maintains certain features and peculiarities of having a variable enclosed volumetric capacity for work-exertion.

Accordingly and by a sort of reciprocal congruence, the four principles of operation as to the importance and need for compression in gas engines and the like which were expressed in 1864 by Beau de Rochas find some applicability to the present devices with regard to obtaining maximized work output efficiency in a so-called four-stroke cycle; these classically being that: (1) there should be a maximum of cylinder volume per unit of cylinder surface; (2) expansion should occur with maximum rapidity; (3) there should be a maximum ratio of expansion; and (4) there should be a maximum initial pressure.

In any event, the mechanical energy involved in the operation of the present fluid-actuated muscle analogue devices insofar as concerns work exertion measurement when operating the assembly so as to have a vertical lifting effect can be gotten from the Equation:

$$W = \int F dL, \tag{1}$$

wherein (taking into account that expandable conduit inflation involves a variable force), W is the work in foot-pounds (i.e., "ft lb") to lift the load (or, as it were, raise a weight), F is the applied force in pounds and L is the distance in feet of the upward movement achieved by the applied force. Of course, the same Equation (1) is applicable when the units of involved measure are converted to Metric System equivalents.

In terms of power (which, broadly-speaking is the time-rate of energy expenditure or work done per unit time), the requirements for operation of the device for any given condition of load movement are calculable from the foregoing. Likewise, the appropriate calculations for measuring work exertion needs to move loads along horizontal or other-than-vertical paths are well known. Nonetheless, given power requirements for given operational needs of the devices are thus reckonable (in the English System) according to the smallest unit of power, which is 1 ft lb/second (i.e., "sec."), or according to the most common unit of power which is horsepower (i.e., "HP"); the singular quantity of which is 550 ft lb/sec. Thus, 1 HP equals 33,000 ft lb/minute (i.e., "min.") and 1,980,00 ft lb/hour (i.e., "hr"). In the Metric System, the smallest unit of work is called an erg which is that done by the force of one dyne acting through a distance of one centimeter. This is also sometimes called the "dyne-centimeter". A larger Metric System unit of work is known as the theoretical joule which is defined as $10^7$ ergs and equals 0.737566 ft lbs. By electrical measurements, what is termed the International or IT joule (although, in practice, the "IT" designation is commonly omitted) has been determined to be equivalent to 1.00032 theoretical joules which equal 0.737798 ft lb. The so-called IT Watt is 1 IT joule/sec.

and the IT Kilowatt is 1,000 IT joules/sec. which equal 737.798 ft lb/sec. or 1.341 HP.

With deference to Heat Units which can become involved in energy requirement calculations for operation of devices pursuant to the present invention, the British Thermal Unit (i.e., the "BTU") has long been defined as 1/180 part of the energy required to raise the temperature of one pound of water through 180° between 32° F. and 212° F. The early investigator, James Prescott Joule, a British Physicist of great renown, determined ca. 1847 that each BTU absorbed very closely approximates each 778 ft lb of expended work in strict accordance with The First Law of Thermodynamics. At an International Steam Tables Conference in 1929, the basic Metric System Heat Unit was redefined in terms of electrical energy units per the Equation:

$$1 \; IT \; \text{Calorie} = \frac{1}{860} \; IT \; \text{Watt hr.,} \tag{2}$$

with the calorie defined as the heat needed to raise one gram of water from 14.5° C. to 15.5° C. From this, making the assumption that the specific heat of water at 15° C. is the same as its average specific heat in the 32°–212° F. range, each calorie can be calculated to equal $3.96832 \times 10^{-3}$ BTU. As the IT Watt is 0.737798 ft lb/sec., the IT Watt hr. is 3,600 times this or 2,656.073 ft lb. From this and for purposes of precise calculations, the value of 1 BTU can be set at 778.26 ft lb. An IT Kilowatt Hour (i.e., "kwh"), accordingly, has a BTU value that very closely approximates 3,412.6 (or 3,413) of the latter English System units.

As to pressure, this is of course the measurement of force per unit area. In the English System (readily convertable to Metric units), pressure is usually given in pounds per square inch (i.e., "psi") or pounds per square foot (i.e., "psf"). By definition, a standard atmosphere is the pressure due to a column of mercury that has a height of 29.92 inches (76 centimeters) at 32° F. This equals 14.6959 psi or 2116.2 psf. The bar, commonly used for (variable) atmospheric pressure, is $10^6$ dynes per square centimeter or 14.5038 psi. Pressure Head (more simply, "head") is the term used to express the pressure due to the weight of a column of liquid. At 60° F., a cubic foot of water weighs 62.36 pounds; and a one foot head of water at this temperature isequivalent to a pressure of 0.4331 psi. A pressure of 1 psi corresponds to a head of 2.035 inches of mercury at 32oF. In very common usage, pressure is seldom given or taken on an absolute basis but noted as gage pressure which is the summation of any excess (or even deficiency) of a fluid under a given gage pressure reading plus atmospheric pressure. The English System units employed to indicate a gage pressure reading are usually "psig" and "psfg".

A useful formula for reckoning, thermodynamically, the involved entropy in the systems of devices according to the present invention is per the classic Equation:

$$dS = \frac{dQ}{T} + \frac{dH}{T}, \tag{3}$$

in which (dS) is the measure of changes of entropy or changes of unavailable energy in a system which occur by: (1) addition or subtraction of heat from the system (dQ); (2) frictional processes in the system (dH); and (3) heat conduction from one part of the system to another; and T is the involved temperature or respective temperatures of operation. In systems made available following device embodimentations of the present invention, heat conduction is usually minimal (if at all) but the (dH) factor is considerable due to expandable conduit inflation effort and other mechanically-caused frictional effects which include load movement(s), etc. Needless to mention, the foregoing Equation (3) also enters into involved power requirement for the operation of any given device as well as pressure requirements therefor in respect of any given motivating-fluid usage. Thus, it has significant didacticity thereabout for present purposes.

There are numerous normally-liquid and normally-gaseous fluids that may be utilized for inflation-pressurization of the expandable conduit member in practice of the present invention. For hydraulic adaptations, water (frequently better for employment when suitably inhibited to minimize its possible corrosive effect) is oftentimes found to be very suitable for the purpose. In pneumatic applications, air is well adapted as a fluid for usage.

In any event, the particular fluid employed must be compatible, physically and chemically, with other components in the system (including, of course, the expandable conduit, the filamentary material in case there is any unlikely contact or exposure therewith and the associated hardware and fittings). Likewise, the selected fluid must be adapted to operate at any temperature that is intended or needed to be experienced for practical operation of the instant robotic biological muscle-analogue devices. While, most often, common room temperature or other usually-encountered ambient temperatures are encountered, there are situations in which the devices may need or be wanted to be operated at and under relatively elevated temperature conditions or, contrarily, in cold situations.

Thus, in place of water, other liquids may be utilized as the fluid for motivating the devices; these including, by way of non-limiting illustration, brine and other solutions (especially in cold temperature service), glycols, mineral oils and so on and so forth insofar as concerns likes and equivalents.

Similarly, other gases may be utilized in place of air when desired or for specialized service in devices made to run with pneumatic motivation. For example, it may be expedient in such cases to employ nitrogen or some other inert gas or gas mixture when it is necessary to employ the device in a flammable atmosphere.

Especially if the involved system is properly insulated for the purpose and/or provided with suitable traps and/or other condensate-handling appurtenances, steam is frequently found to be an excellent fluid for operation of devices in accordance with the present invention. It is, as is well known, a particularly powerful and effective source of good motive power; being especially useful in instances where load-moving requirements are considerable. Of course, devices adapted to utilize steam as the activating fluid must be constructed of materials capable of operationally withstanding whatever heat at an elevated temperature is occasioned by the use of the steam under the given pressure at which it is to be supplied for power provision.

Along this line, there are even situations wherein combustible gases or vapors may be utilized for fluid-actuation of the devices; the expansion products of same being either externally produced and supplied or internally set off within the expandable conduit. Devices made to be so operated, however, must be very carefully designed and engineered with adroit selection of materials of construction and proper utilization of accessory components in order to be capable of successful working capability with such energy sources.

Notwithstanding, there must be incorporated in the devices and for their manner of operation in accordance with the present invention some appropriate means for allowing entry of the expansion fluid (be it liquid or gaseous, including vapors) into the expandable conduit for ballooning thereof followed by withdrawal or other effective disposal of the fluid to permit relaxation of the conduit when its load-moving action is not wanted plus, and in addition, some efficacious means for linking the contractile force of the expanded conduit to the load or object to thereby be impelled or moved.

Although there are numerous ways by which the foregoing necessities may be accomplished, two relatively basic systems capable of utilization are available for pragmatic implementations of the invention. These, namely, are:

1). Assemblies wherein the fluid entry and exit is facilitated and made through the mechanical connecting means associated with the expandable conduit to accomplish load linkage (the same usually being at each terminating end of the conduit); and 2). Assemblies wherein fluid entry and exhaust is provided for via transmission passageways that are independent of the mechanical interlinkage components coupled with the expandable conduit member.

Regardless of which fluid-handling variation is used, it is quite common for a separate conduit or fluid-admitting passageway, port, valve or whatever to be utilized for fluid inlet with another and distinct fluid-outletting means provided for the exhaust. However, there is no requirement for strict reliance on such multiple port or passageway provisions for fluid-handling purposes in the embodimentation of devices pursuant to the invention. Thus, only a single fluid passageway may be utilized for fluid introduction and sequential withdrawal. In such cases, there is no need (although it can conveniently be so done) to position the fluid-handling means at an end of the expandable conduit; it being then possible (and sometimes with advantage) to locate the single fluid duct centrally on or in the expandable conduit. Of course, when double-duct fluid-handling provisions are made, appropriate valving and sealing means must be associated with the assembly to ensure proper entry and exit for controllably effective working of the apparatus. The same applies to single-duct installations. In this and as is readily comprehendible, associated pumping or like or equivalent means for forcing fluid into the expandable conduit and managing its withdrawal are oftentimes necessary to utilize; depending to large extent on the precise techniques utilized for fluid supply and venting. Further in this and as is also readily comprehendible, the fluid-handling systems may follow principles of either closed or open systems, with the exhausting fluid, for example, merely being vented to waste or other non-recoverable discharge or returned for re-use in which event it may require re-pressurization. Also along this line, it is possible to utilize in double-duct systems more than a single inlet port or passageway for fluid admission (with or without multiple outlets) and/or more than a single outlet port or passageway for fluid exhaust (with or without multiple inlets). Similarly, multiple-duct installations may be made to operate the same insofar as concerns fluid-handling as in the above mentioned single-duct systems; which is to say that, regardless of the number of fluid-handling passageway means that are involved and provided, they may be made to operate so as to simultaneously and in co-relationship admit fluid to the expandable conduit at the same time then, through the same fluid-handling ports, subsequently and in unision vent the pressuring fluid for collapse of the expandable conduit member. In unusual cases but where very fine control precision is desired in the ballooning action and effect of the expandable conduit, it is yet further possible to make fluid-handling arrangements capable of bleeding a part of the inletting fluid being forced under pressure into the conduit for contraction thereof; this being sometimes an appropriately applicable technique to follow when too-quick or drastically-sudden movement of the expandable conduit is undesirable or when good pressure control in constant manner of the inletting fluid may, for one or another reason, present a practical difficulty. As is easily appreciable, it may sometimes be expedient to provide the expandable conduit with pressure-release safety valves or "pop-off" vents or the like to avoid undesirable consequences of over-application of inflating pressure in the motivating fluid. These, of course, need not be directly in the expandable conduit but may, alternatively or even in conjunction with such directly-attached conduit placements, be located in the fluid-handling ducts or passageways or suitable and effectively elsewhere in the fluid-handling part of the system.

Mechanically interlinking connecting means that are adapted to provide fluid-handling passageways therein are usually so-formed as to be insertable within one of the open ends of the expandable conduit for sealing connection therewith and to have, integral with their construction, internal passageways for fluid-passage and -conducting purposes. One or two of such connecting means are usual in the systems, depending upon which sort of fluid-handling technique is being utilized. While such connectors can also be made so as to have a cap- or mushroom-like configuration, they generally for most effective attachment with and sealing of the expandable conduit have a shank portion that is insertable (with an appropriate close tolerance) within the open end of the conduit which is to receive the connector. It is frequently advantageous for the insertable shank of the connector to have an encircling protruberance (or shoulder or the like) thereabout so as to magnify the joining and sealing effectiveness it has as a closure for the expandable conduit. Of course, the longitudinally-extending filamentary materials must also be securely-connected and -interlinked with the connecting means to pass on the contractile leverage exerted by the conduit when it is inflated. While there are many ways in which this may be satisfactorily accomplished, one good style for the desired result is to tightly bind (and, if desired, additionally glue or cement) the conduit end in which the shank-provided connector is inserted with an encircling wrapping of tightly wound fibers or filaments—which may or may not be the same as those of the longitudinally-extending placements—and/or to use mechanical clamping means (such as hose clamps or the like) for the purpose with or without the filament end-binding. In and for such fluid-handling connecting means, the fluid-transmitting passageways are usually terminated into the expandable conduit in such a way as to lead generally in the direction of its longitudinal axis or other lengthwise center line with, all in the body of the connector, the external opening of the passageway being directed laterally (usually at right angles) for connection purposes and to avoid interference with the mechanical securing and/or load-moving linkages at either end of the conduit. At the exterior of such a connector (i.e., at its extremity which projects outwardly of or away from the expandable conduit), suitable fastening and/or interlinking means of any desired sort are provided in order to allow attachment of the connector to either the stationery support against which the device works or to the load or object that is to be moved by action of the fluid-actuated muscle analogue device (including pulling on inflation of the conduit and release when the contractability of the conduit is relaxed in an intermediate or total condition of non-inflation or rest). While any desired and satisfactory attachment provision may be employed, such a simple expedient as a hook or eyebolt extension, or the like or equivalent, is oftentimes found to completely suffice for the purpose.

One particularized form of such a fluid-handling connecting means is hereinafter more fully set forth and delineated.

When the involved assemblies have expandable conduit end seals that do not simultaneously handle and pass fluid, they may (by way of non-limiting illustration) be of a simple plug and/or cap design adapted to be inserted within or envelopingly enclose, or both, the open end of the conduit. Protuberances or shoulder ridges and the like on the shank portions (if any) of such connectors or within the skirt portion of a cap or the like (if any) of same are also useful to make efficient sealing of the expandable conduit. With such sorts of connectors, the longitudinally-extending filaments must be permitted to extend beyond the ends of the conduit for inter-linking connections to both the fixed mechanical support of the device and the load-moving coupling means utilized. The degree of filament extension, obviously, depends on the "reach" needed to make the desired or necessary fastening linkages involved. Plug-insert and the like end closures (including cap-like or other formations) may be sealingly-secured in the ends of the conduit in much the same way, if not identically, as that explained for doing the same with the fluid-handling connecting means that can be used.

In this connection, it is possible to have one end of a given expandable conduit closed with a fluid-handling connector and the other end with one not adapted to transmit fluid. This can be done when single-fluid-port techniques are utilized for the admission and withdrawal of the fluid or even, in double-port set-ups, when one of the fluid passageways is located centrally in the conduit to be expanded.

Analogously (and especially when the fluid-handling passageways are provided centrally in the expandable conduit), the conduit, per se, may be fabricated as a totally-enclosed hollow body or made with one or both of its ends open which are sealed shut for operation by straightforward EL welding, cementing or mechanical suturing, stitching, riveting, etc., means with or without the supplementation of added cementing, thermowelding (which may sometimes itself suffice for such a closure), clamping and other shutting and sealing means. In such instances, the longitudinally-extending filaments may then be led at their extending ends out of the secure placement in which they are disposed on or within the conduit or, alternatively (if filament-extension couplings are not desired or appropriate), linking connectors may be fabricated into the conduit ends or securely attached thereto. These may include eyelets and the like worked into the so-sealed ends of the expandable conduit or a suitable furnishment of connectable clamps, jaw-devices and the like or equivalent to secure terminally to the conduit and facilitate other mechanical interlinkage couplings for device securement and load joining to be implemented.

In the following, one particularized adaptation of a non-fluid-handling end closure for the conduit is more precisely detailed. However, self-closed or integrally-end-sealed expandable conduits (regardless of whether they are so fabricated or converted into such condition by integrating end-sealing of an open-ended form) are not more specifically shown or described; the construction and fabrication of such manner of expandable conduit formation being readily apparent and clearly comprehensible upon mere imaginative visualization of same.

(V). Fittings And Accessory Hardware

Much of this has already been included in the disserations precedent hereto, particularly in connection with the above Item (IV). Nonetheless, some supplementation thereof is appropos.

It is evident that, excepting to be functional and lend requisite operability to the robotic fluid-actuated muscle analogue devices and the involved method of motivation pursuant to the present invention, there is no particular criticality in the design and configuration of the various parts and components to be utilized for immediate purposes.

Thus, many equivalents for what has been already mentioned may be utilized. For example, mechanical end connectors may be made with threaded shank portions for screwing into accommodating tap placements made at the ends of tubular expandable conduits or for self-threading sorts of insertions into the conduit; with this, again, being supplementable by cementing, clamping, etc. Fluid-transmitting ducts and passageways must be sized to efficiently accommodate the volumes of fluid necessary for operation under the given conditions of its usage. The same obviously applies to accessory pumps, valving, supply equipment and so forth.

Direction of placement and passage of fluid-handling ducts, etc., is ordinarily of no great criticality. It is only necessary that their courses do not interfere with the mechanical interlinkages involved in the device. Of course, since operation of the fluid-coupled expandable conduit is a dynamic transaction, the fluid fittings and connections made must be of appropriate flexible and/or movable nature to be cooperable with the contractions and extensions of the conduit in operation.

Consistent with the foregoing, apt provision and placement of the fluid-handling accessories for any given installation or usage of a device in accordance with the present invention should also be observed. For example, different and more delicate or considerate arrangements are usually necessary and in order when one of the present devices is utilized in a prosthetic appliance as compared to what may be called for or permissible in some other usage, such as an industrial application. This, by way of some particularization, should contemplate best situating of fluid lines in a given assembly with regard to whether the system is of the atmospheric release variety as contrasted to an enclosed or recycling fluid-handling operation.

When practice of the present invention is made in and for prosthesis, shielding and/or enclosure of the involved device is very frequently provided. However, in other applications this is often a matter of choice even though in some circumstances for safety purposes as regards attendants or for protective purposes as regards the apparatus itself the utilization of shieldings, enclosures and/or other guards or sheathings may be prudent and can even be a necessity. Common sense makes a good dictate of this; even though there are cases in which existing regulations for machinery operation prescribe the need for precautionary utilization of such added equipage.

In most installations, there is no particular need to provide any guiding or alignment-control means to ensure true stroke patterns and reciprocation of the device. On some occasions, however, such accessories may be helpful and, in some instances, even literally mandatory for optimized and most desirable function of a particular assembly establishment. This may be the case when very fine precision is needed in the contractile and releasing stroking pattern of the assembly, regardless of involved size or capacity of the given robotic fluid-actuated muscle analogue device being utilized. It may, however, become more-or-less mandatory in situations wherein the device is disposed and operated in other than vertical or substantially vertical placement; this being particularly so when the involved assembly is of a relatively large and massive construction. By way of further indication of possible necessity for this, some form of guiding stroke-course-motion assistance can be of great help or even requisite when large scale and heavy devices are being used in a more-or-less horizontally operating installation. The guide or stroke-aligning means employed may be of the type analogous to funnelling or engirdling connecting-link position control means to assist and/or ensure the following of a precise travel path for the mechanical connections with the load being moved that are interlinked between the contractible end of the expandable conduit and the object for motive force application that is therewith coupled. Or, they may alternatively or in supplementation of such sorts of movement-pattern regulators be guides associated with the expandable conduit itself. The latter variety may be physically-encompassing slides, sleeves or the like or guide rod or bar elements actually running through the end closures and hollow body of the thereby-supported expandable conduit, or both. Sometimes the confines of prosthetic appliances furnish actual sleeve guiding. If use of such guiding assistance is desirable or necessary, design and construction of satisfactory means to such end is well within the ken of the skilled worker.

A particular form of guide assisting bar associated with the expandable conduit member of a device in accordance with the present invention is hereinafter representatively brought forth.

The materials of construction utilized for the fittings and hardware, and so forth, making up essential componentry or associated accessories of and for the devices of the invention may be selected from wide varieties of substances and products well adaptable for given needs and purposes involved. For any particular selection, consistent with machine design and construction generalities, attention must be paid to such usual factors as strength, weight, fabricatability, resistance to corrosion and/or deterioration (whenever such possibilities may themselves present), wear-resistance and life-expectancy, expectable maintenance (including lubrication) associations, cost, replaceability and so on and so forth. Many of the parts involved can advantageously be made of metals formed by machining, casting, extrusion and other common and known shaping procedures. Various irons and steel alloys, expectably, are useful for such parts; the same being so for light metals and alloys (particularly those of aluminum and/or magnesium), copper and copper alloys, lead and several of the plumbous alloys, etc. Glass and ceramic parts are often quite suitable. And, in many instances, plastics (either thermoformable or thermosetting) are entirely satisfactory, especially when their toughnesses and strengths are adequate and usually lighter weight is an advantage. Most of the plastic goods suitable for use as the longitudinally-extending filamentary materials find nice usages for such parts-provision purposes. Also, many of the so-called "impact-resisting" or "rubber-modified" plastic materials make good choices for such parts constructions; these (besides ABS products) including impact-grades of styrene polymers and copolymers and their likes and equivalents.

Given what is needed or expected, there seldom is any criticality about or difficulty in or of selection as to appropriate materials of construction for utilization in order to make satisfactory provision of the parts and elements involved in the devices of the present invention.

(VI). Generalities

It does merit the emphasis insofar as concerns the practice and embodimentation of devices pursuant to the present invention that the basic principles and limitations of: fluid and gas engineering and associated thermodynamic and other physical laws and principles; natural rubber and other El products including solid articles of manufacture therefrom and latices and other formulations for adhesive and other purposes therewith; EL's and latexes insofar as relates to manufacturing and handling thereof, including polymerization procedures for their preparation; filamentary and funicular goods and products of natural, artificial or synthetic nature and their fabrication and use; fluids of liquid or gaseous nature (including steam and other vapors) and the handling, use and application thereof in and for hydraulic and/or pneumatic power supply purposes and applications; machine building and operation procedures and techniques; machine and machine parts design and implementation(s) for the presently-contemplated purposes; suitable materials of construction for given utilization requirements; and so forth are so widely comprehended by those skilled in the art that greatly elaborated detailing and/or fundamentals-explanation of all the basics thereof and/or above and beyond the limited explanations and indications here put forth is not herein made nor attempted—the same being unnecessary for thorough understanding and recognition of the advance possibilitated for achievement and realization by and with the present robotic biological muscle-analogue development that involves fluid-activating procedures and its outstanding improvement potentials and realizations that are according to and in keeping with the present contribution to the art.

SUMMARY OF THE INVENTION

The present invention, in its genesis and as derives from the discovery on which it is based, concerns, inter alia, the indicated novel means and mechanisms and the procedural technique for furnishment of a robotic, fluid-actuated muscle analogue which, as an improved contractile device for the provision of motive power, comprises (broadly speaking and more or less): an expandable central conduit characterized in exhibiting end-to-end contractibility when inflated (or "balloned") from a position of undistended and non-foreshortened rest by admission or interjection into its hollow center of an activating liquid or gaseous fluid under pressure; at least one and generally a plurality of longitudinally-extending filaments or the like fibrous strandular materials fixedly secured and positioned peripherally in or on the wall structure of said expandable conduit and so laid thereabout (including in wall-contained dispositions) as to run at least substantially parallel with the axis or other center line of said conduit and to extend at least from end to end thereon and/or therewithin; means associated with said hollow conduit for introducing and exhausting fluid into and from the void interior space of the conduit and containing same therewithin to maintain said conduit at any desired degree or to any appropriate extent of laterally-directed inflation, whereby the effective longitudinal end-to-end length or span of the attached filamentary material is lessened and foreshortened relative to the expanded condition of the conduit under any given degree of its inflation and in correspondence to conduit-contraction upon inflation; and associated mechanical interlinkage means for anchoring one of the longitudinal ends of the conduit to a stationary support therefor (which beneficially may have direct or indirect coupling with the terminating extremity of said attached longitudinally-extending filamentary material concluding at that end of the conduit) and for fastening directly or indirectly through said longitudinally-extending filamentary material attached on the conduit at or about the contractably-moving end of said conduit with a load or object to be moved or impelled upon and by operation of the device when motivated.

By and large, the various suitable materials, means, sub-assemblies and overall assemblies, sub- and overall procedures, plus other implementing components, facilities and associations for utilization, as well as many working details and usage indications, embodimental instructions and plans and other specifics of the invention have already been propounded in the foregoing Specification; the same being additionally and materially supplemented by the dispositive delineations which follow.

In this and as appears from what heretofore has been disclosed as well as will be discernible in and from the additional revelations that follow, still other features and implementations of beneficial import and salience above and beyond the simplified rudiments immediately-above-stated are advantageously combinable in and made integral part(s) and portion(s) of the principal and above fundamentally-described beneficial way of providing and using the here-contemplated robotic fluid-actuated muscle analogue device(s) and technique(s).

ILLUSTRATED EXEMPLIFICATION OF THE INVENTION

The invention is pictorially demonstrated in and by the eighteen (18) views in and of the accompanying Drawing which, for simplicity and convenience, are largely illustrated in mostly schematic and/or fanciful manners of representation including, also for purposes of enhanced clarification, purposefully exaggerated portrayals insofar as concerns involved dimensionalities, etc., but in all of which to the greatest extent possible there is utilized the same reference numeral designations for like and/or similar parts, elements and components wherein, as they are to be taken in conjunction with the following Specification:

FIG. 1 is a front (or side) elevational view in somewhat fanciful portrayal, broken apart and partly in section, of one possible form of device in accordance with the present invention shown in vertically-upright disposition wherein the end connectors and sealers for the expandable conduit are, in and of themselves, of the simultaneously built-in fluid-handling variety;

FIG. 2A is a schematic cross-sectional view of one manner of construction of a tubular expandable conduit for utilization in devices according to the invention demonstrated in this involved showing in both an unexpanded, "at rest" posture and also, by means of phantom outlining, as the outer peripheral wall of the conduit would appear when inflated or "ballooned" in use;

FIG. 2B is a schematic cross-sectional view of an out-of round (or oval or "bladder"-like) form of expandable conduit member adaptable for use in practice of the present invention;

FIG. 2C is a schematic cross-sectional view of another form of expandable conduit member having a generally square polygonal configuration;

Figure 9A:
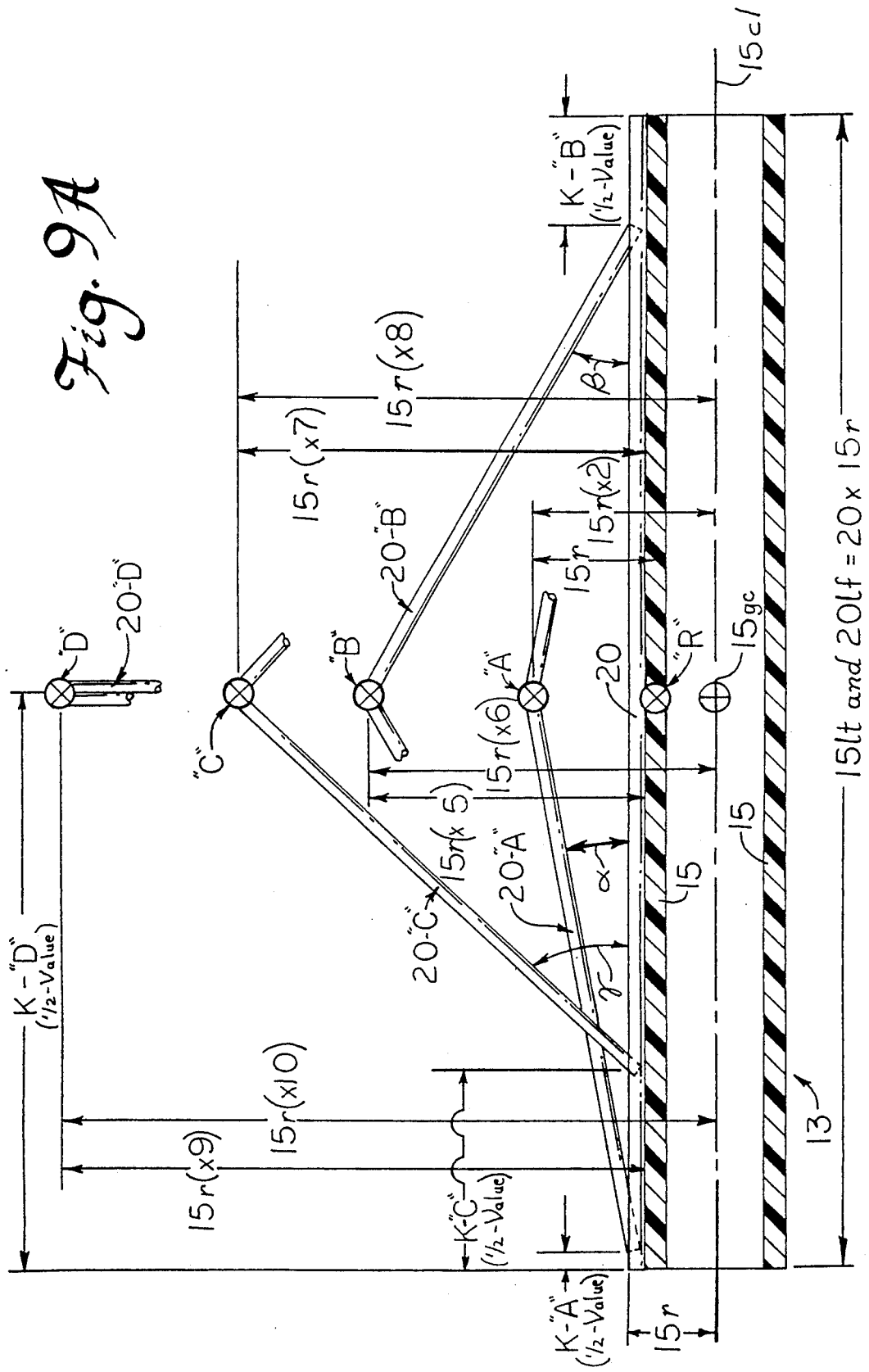

FIG. 3 is another schematic, cross-sectional view of another manner of construction of an expandable conduit member (illustrated as being tubular in this showing) for utilization in devices according to the invention wherein the longitudinally-extending filamentary materials are mechanically embedded within the wall portion of the conduit much in the manner of tire cord or other internal strandular reinforcements for hosing and the like mechanical rubber goods, including beltings;

FIG. 4A, also a schematic cross-sectional view sort of showing, depicts a system for associating the longitudinally-extending filamentary materials mechanically in the outer periphery of the expandable conduit by emplacement or embedment in receptive, longitudinal grooves or channels therefor in the conduit wall (again, for illustrative purposes, being represented as of a tubular conduit construction);

FIG. 4B is a fanciful side-elevational view of the expandable conduit type of structure shown in FIG. 4A which illustrates the mechanically-associated, longitudinally-extending filamentary materials embedded in the outer wall slots of the conduit and also illustrating a fixing or fastening means for maintaining the filaments in position when they are so incorporated in the conduit construction;

FIG. 5, analogous to the demonstration of FIG. 1, is a front (or side) fanciful elevational view, broken apart and partly in section, of another possible form of device in accordance with the present invention and also shown in vertical upright disposition wherein the sealing end connectors for the expandable conduit are not, per se, built or adapted for internal fluid handling;

FIG. 5A, in a fanciful, side-elevational view schematic portrayal, demonstrates one manner of accessory fluid-handling arrangement possible in a device pursuant to the invention wherein the sealing end-connectors are integrally provided with built-in fluid-passing and -controlling capabilities;

FIG. 5B is another fanciful side-elevational view schematically portraying a varied arrangement for fluid-handling accessories possible to utilize in a device in keeping with the invention wherein the sealing end-connectors are also made to in and of themselves be able to pass and control fluid into and out of the expandable conduit member of the contrivance;

FIG. 5C, in schematic side-elevational view presentation, shows one sort of guide bar means built to transpierce the expandable conduit member longitudinally for its physical support and that of the overall device during operation thereof, especially when disposed out of a vertical dispositioning alignment;

FIG. 6, in a side (or front) elevation view portrayal, demonstrates schematically a device pursuant to the invention of the general type illustrated in FIG. 1 when it is in an inflated or "ballooned" condition and which also illustrates the contractability of the device during operation when it is being actuated under internal fluid pressure application;

FIG. 7 is a cross-sectional view taken along the Line 7—7 in FIG. 6 demonstrating the fluid-filled expandable conduit member in an inflated or "ballooned" condition when injected with fluid under sufficient pressure to expand the conduit out of its (also phantomly-illustrated) normal, non-distended condition of rest;

FIG. 8 is a side (or front) elevation view somewhat analogous to the showing of FIG. 6 which demonstrates a device in accordance with the present invention having engirdling constrictions provided along the length of the expandable conduit member which serve to materially magnify the contractability potential of the device, indication of a relatively-possible extent of which is also brought forth in this view;

FIG. 9A is a schematically-fanciful view, partly broken away and partly in section, which geometrically demonstrates contractability extents of an expandable conduit member in a device according to the invention according to the degree or extent of fluid pressurizing internal inflation thereof;

FIG. 9B is a totally schematic illustrational view depicting applicable contractile force actions caused by central lateral depression of a longitudinally-extending element which, by good analogy, demonstrates the behavior of an expandable conduit member in a device pursuant to the invention when its walls are distendingly-inflated by internal fluid pressure centrally introduced therein for operational activation of the conduit;

FIG. 9C is a view showing a typical right triangle to bring specifically forth the classical geometrical relationships therein involved and which are therewith associated; and FIG. 10 is a symbolic and schematic elevational view, partly broken away, demonstrating a prosthetic appliance equipped with and motivated by a device in accordance with the present invention which, with precise particularization thereabout, is a fluid-actuated muscle analogue system that is in full keeping with present concepts.

For expedience and enhanced clarity of: associated parts and components or elements; sub- and overall-assemblies; certain companion movements, functions and so forth; and results; reference of a primarily eclectic nature is now thereto had to all such predominant cooperative componential features and consequences of their operation as they appear throughout the accompanying FIGURES included in the Drawing with an explanation thereof in the following catalogued elucidation of same as they are identified by their respective reference number and/or letter designation(s) {i.e., "Ref. No(s)."} wherein and in the below-presented descriptory of same an asterisk(*) accompanies any given Ref. No. which is intended to convey a general designation (e.g., appearing by having an arrowheaded lead line for the demonstration or specific pointing out of the part or thing to be generally illustrated) in any of the views of the Drawing in which said Ref. No. occurs.

| Ref. No(s). | Description With Relevant Corollary Explanation |
| --- | --- |
| 11* | A robotic, fluid-actuated, muscle analogue device *in toto* or in any partial or otherwise varied viewing of same that is in accordance with the present invention and which, per its own capabilities in assembly and by and as a result of application of the theoretics of its operability, is well adapted for many load-moving purposes including, without limitation, in and for energization of prothetic devices as well as for many of a wide variety of industrial utilizations and the like or equivalent purposes such as in or in connection with instrumentation and/or instrumentating appliances and so on and so forth. The expandable, usally of an EL material, conduit member or component of a device pursuant to the invention. |
| 13* | |
| 13W* | The interior wall surface of the expandable conduit member, especially when the latter is in an uninflated or "at rest" position in which it in not under fluid-activating motivation or influencing. |
| 13X | The expansively "ballooned" or inflated situation or position assumption as a result of fluid-activation of the expandable conduit member 11 (particularly shown in schematic depiction by the heavy dot-dash line representation in FIG. 2A of the Drawing). |
| 13NR* | A non-tubular or out-of-round cross-sectioned expandable conduit member (shown only in FIG. 2B of the Drawing). |
| 13SQ* | A square or other polygonally cross-sectioned expandable conduit member (shown only in FIG. 2C of the Drawing). |
| 13MX* | As is shown only in FIG. 8 of the Drawing, an expandable conduit member having multiple, intermediate constrictions or circumscribing constrictive bindings along its end-to-end length which is illustrated in said FIG. 8 in an inflated, activated-under-fluid-pressurization condition. |
| 14M* | As is shown only in FIG. 3 of the Drawing, an expandable conduit member wherein the associated longitudinally-extending filamentary material is provided (by composite molding techniques or otherwise) within the wall structure of the conduit. |
| 14S* | As is shown in FIGS. 4A and 4B of the Drawing, an expandable·conduit member wherein the associated longitudinally-extending filamentary material is provided by a more-or-less mechanical emplacement or holding in accommodating receptacle grooves or channel slits in the outer peripheral wall portion of the inflatable EL structure of the expandable conduit member 14M. |
| 15 | The inflatable rubber or other EL tube or the like component, *per se*, of the expandable conduit member or or part of a device in accordance with the present invention. |
| 15M | As is shown in FIG. 3, the EL tube constructed for formation of the expandable conduit member by having the longitudinally-extending filamentary material centrally-embedded or -contained therein. |
| 15NR | The out-of-round (ovally or otherwise) bladder component of the expandable conduit member (FIG. 2B). |
| 15SQ | The square (or like polygonal) EL structure of an expandable conduit member (FIG. 2C). |
| 18 | A gum rubber or other EL layer for bonding the longitudinal setting emplacement of filamentary material securely on the surface of the inflatable EL component in order to provide the expandable conduit |

| Ref. No(s). | Description With Relevant Corollary Explanation |
|---|---|
| | member of a device for use in the practice of the present invention. |
| 19 | The grooves or channel slits in the outer peripheral wall of the inflatable EL component to accommodate mechanical placement and holding of the longitudinally-extending filamentary material in and for the expandable conduit member, the same being particularly illustrated in FIGS. 4A and 4B of the Drawing. |
| 19C | Catch holes or socket formations in the grooves 19 to assist in the mechanical securement of the longitudinally-extending filamentary material emplacements (FIG. 4B). |
| 20* | The longitudinally-extending filamentary material inclusion of an expandable conduit member embedded for secure attachment to the EL tube or equivalent inflatable component in the gum rubber or other EL or like or equivalent layer employed for filament affixation within (or upon) the expandable conduit structure. |
| 20M* | The molded-in or otherwise centrally-embedded longitudinal filament components of an expandable conduit member (as is shown in FIG. 3 of the Drawing). |
| 20G* | Mechanically-mounted and -maintained longitudinally-extending filamentary material components (shown in FIGS. 4A and 4B of the Drawing). |
| 20P | Knots, mechanical protruberances or other bulges or enlargements of mechanically-emplaced longitudinally-extending filamentary material components to maintain same in the lock-catch enlargements 19C per the illustration of same in FIG. 4B of the Drawing. |
| 20F* | As is shown only in FIG. 5 of the Drawing, the free (i.e., non-secured in the expandable conduit member) extending ends of the filamentary material emanating beyond the terminal portions of the expandable conduit for making connections to install the device in position and for and with the load to be therewith moved especially in situations in which the expandable conduit end-closing fixtures are not of the built-in internal fluid-handling variety. |
| 22 | The central void or hollow space within the expandable conduit member for containment of the inflating fluid therein injected or introduced. |
| 25* | An eyebolt fixture adapted to simultaneously close and seal the open ends of the expandable conduit member and pass activating fluid thereinto and therefrom via integral passageways therein built and provided. |
| 25S | The shank portion of an eyebolt piece of hardware of the fluid-handling assembly sort of such fitting (illustrated only in FIG. 1 of the Drawing). |
| 25P | As is also shown only in FIG. 1, the protuberance or shoulder bulge along the shank portion 25S of the eyebolt style fluid-handling fitting or fixture 25. |
| 26 | The piping or the like structure for fluid handling purposes that connects and is associated with the eyebolt fixture hardware part 25. |
| 27* | Fluid transmitting and -conveying passageway openings or ducts in the piping (or equivalent) structure(s) 26, around the ends of the expandable conduit member to assist in good closing securement of the sealing hardware fixture piece(s) or part(s) therein placed which, as has been indicated, may be supplemented or replaced by hose clamp and/or the like or equivalent locking seals or bandings (not shown). |
| 30 | As is portrayed only in FIG. 5 of the Drawing, an insert bushing or the like style of end closure fitting for the expandable conduit of the sort which is not adapted to simultaneously provide, *per se*, mechanical interlinkage coupling means directly with and from the terminating, contractively-moving longitudinal end portions of said conduit member. |
| 31 | As is depicted in FIG. 5C of the Drawing, a guide rod or bar longitudinally transpiercing the expandable conduit member without any showing along with this of "0"-ring or the like seals to go with the bar for sealing purposes or sleeves or other possible equivalent and/or accessory guiding means. |
| 32 | A rivet- or washer-like bolting connector to which the free ends 20F of filamentary material are tied or otherwise secured to provide the coupling means for mechanical interlinkage(s) of the device (FIG. 5). |
| 33 | A connecting linkage piece (equivalent, e.g., to a bolt shank or the like) for operable mechanical intercoupling of the device in a working position (shown only in FIG. 10). |
| 35 | A fluid control valve installation (FIGS. 5A, 5B and 5C). |
| 36 | Shown only in FIG. 5A, a cap to seal off the piping connection in a fluid-handling eyebolt fixture desired to be utilized devoid of its fluid-passing and -transmitting feature, as when even with such hardware only a single port is wanted. |
| 40* | As is illustrated only in FIG. 7 of the Drawing, the interjected fluid contained in the central hollow or void space of the expandable conduit member under inflationary pressure which causes its contractile inflated ballooning (with, in the same FIG. 7, the original uninflated or "at rest" position of the interior wall surface 13W of the expandable conduit being portrayed by dotted line representation). |
| 45 | The constrictive bindings or segmental inflation-hindering wrappings along the length of expandable conduit member 13MX (FIG. 8) which serve to magnify the constrictibility of the expandable conduit member when it is under fluid-activation |
| 50 | A double-ended arrow denoting the normal length of an ininflated expandable conduit member in "at rest" position (FIG. 6). |
| 50M | Another bidirectional (i.e., double-ended or double-headed) arrow shown in FIG. 8 to indicate normal length extension delimitation of an along-its-length constrictively-bounded or -cinched expandable conduit member 13MX when it is in an "at rest", uninflated, maximumly-extending position. |
| 50XC | The foreshortened length of the expandable conduit member 13X when it is in an inflated and ballooned condition so as to have end-to-end contraction thereof caused, as is demonstratively measured by the so-identified bidirectional arrow in FIG. 6. |
| 50MXC | The bidirectional arrow indicating the diminished length in inflated, contractability-causing position of the end-to-end constrictively-bound expandable conduit member 13MX (FIG. 8). |
| 50CD | The contractive take-up distance/stroke or degree of foreshortening of the expandable conduit member 13X when it is in an inflated condition of ballooned expansion (FIG. 6). |
| 50MCD | The relatively greater (by comparison to the dimension 50CD illustrated in FIG. 6) contractive take-up distance or degree of end-to-end foreshortening of the constrictively-bound expandable conduit 13MX, as is shown in FIG. 8 of the Drawing demonstrating the enhanced stroke so achieved. |

NOTE - the immediately-following twenty-one (21) Ref. Nos. are of singular pertinence to the illustration of FIG. 9A of the Drawing.

| Ref. No(s). | Description |
|---|---|
| 15r | The radius of an expandable conduit member which, by way of appropriate illustration, is tubular and, for purposes of illustration, may be considered to have a diameter in total O.D. of, say, 3 units of any desired unit of measure (such as 3 centimeters {cm.}) so that, in such instance, the measurable radius 15r from the outer circumference of said conduit cirumenveloping the therewith included longitudinal placement of filamentary material 20 is 1½ cm. |
| 15lt and 20lf | The length of the uninflated expandable conduit member 13 and the EL tube substrate 15 of which it is comprised, as well as the length of the emplaced filamentary material (presumed, for purposes of the illustration, to be of a non-extensible nature) in any "at rest" position or condition of partial or total (to the greatest permissible extent) inflation or ballooning of the expandable conduit member (presuming with this, also for purposes of the illustration, that the expandable conduit is of a non-burstable nature and has a more-or-less regular and directly proportionate relationship between extent of expansion under fluid-activation and corresponding length-shortening contraction of the conduit under inflative pressure), so that if the uninflated expandable conduit length and correspond- |

-continued

| Ref. No(s). | Description With Relevant Corollary Explanation |
|---|---|
| | ing length of the longitudinally-extending filamentary material is, say (and likewise for purposes of the illustration), 30 cm./then both 15lt and 201f equal 20 × (15r). |
| 15cl | The center line of the EL tube component 15 of the epandable conduit member 13. |
| 15gc | The exact geometric center of the involved tubular expandable conduit member. |
| "R"* | A Point in the wall of the tubular expandable conduit member situate exactly mid-way of the uninflated, "at rest" length thereof. |
| "A"* | The Point to which said Point "R" is elevated when the expandable conduit member is inflated to twice its orginal diameter so that the distance between 15cl and Point "A" is 2 × (15r). |
| "B"* | The Point to which said Point "R" is further elevated when the expandable conduit member is inflated to six-times its original, "at rest" diameter so that the distance between 15cl and Point "B" is 6 × (15r). |
| "C"* | The Point to which said Point "R" is yet further elevated when the expandable conduit member is inflated to eight-times its original, "at rest" diameter so that the distance between 15cl and Point "C" is 8 × (15r). |
| "D"* | The (completely hypothetical and, pragmatically, only imag- inarily possible when non-extensible filamentary material attachments are employed) Point to which said Point "R" is still further elevated when the expandable conduit member is inflated to ten-times it original, "at rest" diameter so that the distance between 15cl and Point "D" is 10 × (15r). |
| 20-"A" | The disposition of the longitudinally-extending filamentary material running through Point "R" when that Point is trans- posed by inflation of the expandable conduit member to assume the Point "A" position. |
| 20-"B" | Likewise for filamentary disposition but when "R" is in the Point "B" position. |
| 20-"C" | Likewise for filamentary disposition but when "R" is in the Point "C" position. |
| 20-"D" | Likewise for filamentary disposition but when "R" is in the Point "D" position. |
| α | The angle (i.e., " ") assumed between the longitudinally-extending filamentary material length when disposed in its 20-"A" posture with respect to the line parallel to the center line 15cl of the filament 20 (when the expandable conduit is uninflated and "at rest") as, coincident with the ballooning by fluid-activation of the expandable conduit member, "R" assumes the Point "A" position. |
| β | Analogous as to the assumed by the filamentary material length in its 20-"B" disposition when "R" assumes the Point "B" position. |
| γ | Again analogous to the assumed by the filamentary material length in its disposition marked as 20-"C" when "R"assumes the position of Point "C". |
| K-"A" | The half-length contractive take-up or foreshortening of the expandable conduit member when so inflated that the longitudinally-extending filamentary material length is extended at α, presuming in all of this that the angulation followed by the filamentary material follows a linear path and ignoring curvature in the wall of the expandable conduit member during its ballooning (which presumption, at least for the intended illustrative purpose, is at least approximatively correct and sufficiently accurate for the purpose). |
| K-"B" | The corresponding half-length contractive take-up of the expandable conduit member when so inflated that the filamentary material length is extended at β, taking into account in this (as are also the cases for the above-defined contraction distance K-"A" and the below-defined contraction distance K-"C") that the total contraction of the expandable conduit member in this condition of ballooned inflation is actually 2 × (K-"B"). |
| K-"C" | The also corresponding half-length contractive take-up of the expandable conduit when the filamentary material is so disposed due to conduit inflation as to lie at γ. |
| K-"D" | The hypothetical complete contractive take-up of a maximumly inflated expandable conduit member so ballooned as to upwardly extend the filamentary magerial at a full 90° angulation. |

NOTE - the immediately-following sixteen (16) Ref. Nos. are of primary relevance to the depictions of FIGS. 9B and 9C of the Drawing.

| Ref. No(s). | Description With Relevant Corollary Explanation |
|---|---|
| 51 | Bendable upright stands or posts (such as, by way of illustration, tree trunks or the like) between which a non-extensible cord or rope may be horizontally tied. |
| 51b | As depicted in phantom (dotted) outline, the stands 51 inwardly bent mutually towards one another by depression of the interconnecting non-extensible line secured there-between. |
| 52 | The non-extensible line tied between stands 51. |
| 52d | The line 52 shown shoved (or forced) downwardly in phantom (dashed) outline. |
| 53 | A dot-dash line indicating the limit of/any given up to a maximum depression of the cord 52. |
| d | The depression distance of cord 52 when displaced to its maximum limit against line 53 upon application of a depressing force at its center point. |
| F | Arrows indicating the direction of force to depress the cord 52 and cause inwardly-directed bending of the stands 51. |
| $T_1$ and $T_2$ | The tensile forces or tensions exerted upon the application and of force F to depress the cord 52. |
| θ | The of depression of the cord 52 upon application of downwardly-depressing force F. |
| X, Y & Z | The 's of a typical right triangle from which geometric functions and relationships are derived and determined. |
| c | The hypotenuse of the triangle. |
| b | The side of the triangle adjacent X. |
| a | The side of the triangle opposite X. |
| 60* | A prosthetic, artificial arm contrivance that is equipped with and utilized for its energization a robotic, fluid-actuated muscle analogue device in accordance with the present invention, as is illustrated in FIG. 10 of the Drawing. |
| 60B | The biceps portion of the device 60. |
| 60F | The forearm part of the device 60. |
| 60H | The hand part of the device 60. |
| 61 | A pivot or hinge inclusion at the elbow section of the prosthetic device 60. |
| 70 | A directional arrow showing the upwardly-swinging direction of motion of the device 60 upon contractive activation of the fluid-actuated muscle analogue 11 therein included. |

With an overview of the foregoing disclosure and instructional parameters and revelations being maintained, the subsequent portion of this Specification now turns to yet-further particularized explanations and specifically-illustrated embodimentations and applications of practice of the present invention.

ADDED EXPOUNDATION PLUS WORKING EXEMPLIFICATION OF THE INVENTION

Amongst the serendipitous beneficiations realizable in practice of the present invention is the indicated fact that, upon ballooning inflation of the expandable conduit member of the device so as to effectuate its contractibility along its lengthwise, end-to-end disposition, the pulling tractile force exerted and achievable in this (by any weight per unit work output measure of any given device pursuant to the invention that is involved) can literally be of a tremendous order of magnitude; this being especially the case during the initial phases of fluid-activated inflation of the conduit.

Amplification and demonstration of this is now had with coincident retroduction to FIGS. 9A, 9B and 9C of the Drawing. These views, particularly the illustration of FIG. 9B, emphasize and highlight the physical involvements and procedures which enable practice of the present invention to be capable of making available for whatever desired purpose is intended to therewith be utilized the powerful contractive force possibilities of which the robotic, fluid-actuated muscle analogue devices of the present invention are possessed to such an advantageous and remarkable degree.

Looking preliminarily in connection with this to FIG. 9C of the Drawing, it is worthwhile to recall and restate certain of the derivations of natural sine and cotangent values per the ancient and classic Equations therefor, namely and to wit:

$$\sin X = \frac{\text{opposite side}}{\text{hypotenuse}} = \frac{a}{c}; \text{ whence } a = \sin X \cdot c; \qquad (4)$$

and $$\cot X = \frac{\text{adjacent side}}{\text{opposite side}} = \frac{b}{a}; \text{ whence } b = \cot X \cdot a. \qquad (5)$$

Now then and with the taking into particular account of the illustration of FIG. 9B of the Drawing, one may consider for purposes of contemplative comprehension a simple rope or the like cordage that is tied between two trees (or like or equivalent laterally bendable stands or posts) with the hypothesis therewith attached and as has been mentioned that the rope is of a non-extensible-under-tensile force character. As should be readily apparent to anyone with any experience concerning such lashings, it requires very little physical effort or force to depress the rope at its midpoint between the two tree trunks or the like. Yet, any such depression institutes a very powerful exertion of force on the rope insofar as pertains to its pulling-together potential and capability of bending the attached tree trunks. This, obviously and very positively, tends to pull the trees together in the mutually-crooked-one-towards-the-other direction. The involved tensile force is at a maximum when the inter-connecting rope is initially deflected; thereafter decreasing to a minimum when the angle of the rope at the midpoint (i.e., $\phi$, $\theta$) increases to the 90° end point therefor.

The involved reaction and effect is all by the following composite and generalized Equation expressive thereof:

$$\text{(Presuming and in the cases where } T_1 = T_2\text{)} \qquad (6)$$
$$\text{Then: } 2T \sin \theta = F, \text{ and}$$

$$T = \frac{F}{2 \sin \theta}, \text{ all as}$$

$$\theta \to 0 \text{ and } T \to \infty.$$

The above particularly-demonstrated action and result of rope depression nicely points out what happens to the longitudinally placed filamentary materials incorporated into the expandable conduit member construction in devices in accordance with the present invention when and as the said expandable conduit is inflatingly ballooned under the influence of internal fluid-activation so as to deflect the associated longitudinally-extending filaments out of a straight line disposition in conjunction with the conduit when it is at the unexpanded and "at rest" position.

As has already been amply brought forth, the initial force that is available for the power stroke expectable and coming about by operation of a device in accordance with the present invention depends, inter alia, upon: the actual involved length of the associated longitudinally-extending filamentary material placements made in conjunction with the expandable conduit member; the internal surface area (i.e., that of the interior wall portion 13W) of the expandable conduit member itself; and, of course, the operating and impulse-effective pressure of the working fluid interjected into the central void space of the expandable conduit member (minus, as must be reckoned, that portion of the work energy available in said fluid needed to inflate the expandable conduit, per se, under "no load" conditions) in order to cause contractile ballooned inflation of the conduit member which ultimately exerts the involved tractile effort thereupon. As is readily comprehensible, the decrease in leverage available as the longitudinally-extending filamentary material is deflected during a contraction upon inflation of the expandable conduit member is, at least to some degree, offset by the increase undergone in the actual internal surface area of the expandable conduit as it is (and after) being ballooned by the therein-introduced fluid-for-activation under pressure.

Introspection of FIG. 9A of the Drawing, along with the following superficial explanations thereof, further brings out the contractability possibilities available upon inflation of an expandable conduit member by fluid-activation thereof in devices made and operated in accordance with the present invention. As has been indicated, this illustration represents and at least roughly displays the degree or actual measure of contraction (i.e., "K") that can be expected to be experienced with and upon any given level of diameter-increasing inflation of the involved expandable conduit.

For the involved calculation, the following Equation is applicable:

$$K = 2 \times \cot \angle(?) \times h_a \times \kappa LT, \qquad (7)$$

wherein: K is as above defined; $\angle(?)$ is the involved angulation in question of the filamentary material upon inflation of the expandable conduit member (such as $\alpha$, $\beta$ or $\gamma$ in FIG. 9A of the Drawing); $h_a$ is the actual radial height of elevation of any mid-point (such as "R" in FIG. 9A) in the wall of the expandable conduit member upon inflational ballooning thereof, which height measurement—with the assumption that the conduit employed exhibits an ideally-uniform resistance to expansion along its length so that under internal fluid-actuation the maximum extent of expansion occurs midway along or at the half-length, of the conduit—is that of the given mid-point when the conduit is in an expanded condition less the original uninflated radius of the conduit; and LT is the "at rest" and unexpanded length of the expandable conduit itself as well as that of the therein-associated longitudinally-extending filamentary material when measured in conduit end-to-conduit end emplacement with the conduit in and uninflated, "at rest" condition.

Working with the illustrations made in FIG. 9A of the Drawing and using a tubular expandable conduit of the physical size (i.e., 3 cm. O.D. and 30 cm. length) as given with the foregoing explanation of that FIGURE, the following demonstrated contractability stroke measurement anticipatabilities are calculable per said Equation (7).

Contractability Demonstration

With "R" at the Point "A" position, the value of α is obtained by the following figuring (assigning, as is indicated in the foregoing, a 1×15r or 1.5 cm. value to "a" and a 10×15r or 15 cm. value to "c" which is the half-length of the filamentary material providing the involved hypothenuse per FIGS. 9C and 9A, respectively, of the Drawing):

$$\angle a \text{ taken from } \sin\frac{a}{c} = \frac{(15r)}{10(15r)} = \frac{1.5(\text{cm.})}{15(\text{cm.})} =$$

$$0.1 = / \sim 5.7 - 5.8°$$
(appropriately-intermediate)

Then:
"b" (or the measure of the base of the involved triangle) =
$a \times \cot \alpha = (15r) \times 9.8448 = 9.85 \times (15r)$ or, multiplying 1.5 cm. × 9.8448, = 14.7672 cm.

Accordingly, half of the total contraction involved (obtained by subtraction of the value of "b" from the half-length of the uninflated expandable conduit member) is 0.15(15r) or 0.23 cm. The total contraction of the inflated expandable conduit member (or the full value of "K") is thus 0.30(15r) or 0.46 cm.

From this, the percentage of involved contraction based upon reduction in length of the foreshortened expandable conduit when in the inflated condition represented by "R" being at Point "A" (in FIG. 9A of the Drawing) as compared to the uninflated, "at rest" length of the conduit may be arithmetically reckoned by a solution involving:

$$\% = \frac{0.30(15r)}{20(15r)} \times 100 = 1.5\% \text{ or } \frac{0.46 \text{ cm.}}{30 \text{ cm.}} \times 100 = 1.5 + \%.$$

Repeating the preceding calculations to determine the involved values when "R" is elevated upon inflation of the expandable conduit to assume Point "B", the resulting quantities are found to be: 30° for β; 9.8805×(15r) or 12.991 cm. for "b"; 1.33×(15r) or 2.01 cm. for ½ K.; and 13.3+% for the percentage contraction figure.

Again going through the same calculations to find the values applicable when "R" is at Point "C", the findings are: 44.5° for γ; 7.1232×(15r) or 10.6848 cm. for "b"; 2.82×(15r) or 4.32 cm for ½ K.; and 28.8% for contraction percentage.

In this connection and as is readily apparent, the indicated values may also be mathematically obtained, amongst other procedures possible to employ, by application of the ancient and well known Pythagorean Proposition (or Theorum).*
(*See FOOTNOTE)

The following experimentations still further illustrate the invention.

First Illustration

A basic contractile device according to the robotic, fluid-actuated muscle analogue systems of the present invention was built and operated.

For the accomplishment of this, a piece of gum rubber tubing having a 0.5 inch (i.e., "in.") I.D. (1.27 cm.) and 0.75 in. (1.905 cm.) O.D. was cut to a length of 15½ in. (38.10 cm.). The so-sized gum rubber tubing was then coated with a thin layer of rubber by brushing its exterior surface with natural rubber latex which was then allowed to (air) dry. A number of lengths of a braided "DACRON" (Reg. TM) polyester cordage were then prepared. These were made into 24 in. (60.96 cm.) individual sections by the cutting thereinto of a 50 lb. test (or class) fishing line material made out of the indicated polyester. The cut fishing line sections were employed as the longitudinally-extending filamentary material (or filaments) for fabrication of the expandable conduit member for the device with the gum rubber tube.

One of the cut filaments was carefully positioned longitudinally and parallel with center line upon the outer surface of the latex pre-treated tube. A thin layer of natural rubber latex was then brushed on over the positioned filament and allowed to dry in air. This firmly secured the filament to the gum rubber tubing.

FOOTNOTE

As an illustration of this and to show a different particularization for the calculation, the following mathematical derivation may be utilized, viz, $$\cot \angle (?) = \frac{b}{h_a}, \text{ with} \qquad (7a)$$

$$b = \frac{LT - K}{2}, \text{ so that then}$$

$$\cot \angle (?) = \frac{LT - K}{2h_a}, \text{ and}$$

$$LT - K = 2 \cdot h_a \times \cot \angle (?), \text{ and}$$
$$- K = 2 \cdot h_a \times \cot \angle (?), \text{ resulting in}$$
$$K = LT - 2 \cdot h_a \times \cot \angle.$$

NOTE: The symbol "$h_a$" obviously represents the height of side "a" opposite angle "X" in the triangle drawn out of FIG. 9C of the Drawing, with said angle being for any given case the angle "$\angle (?)$" used in the above Equation (7a) as well as in the foregoing Equation 7 of the first-demonstrated calculation;

Applying the foregoing to calculate, by way of illustration, the value of "K" for Position "B", one proceeds per the below-given figuring, e.g.:

$$\cot 30° = 1.732, \text{ and}$$
$$K = LT - 2 \cdot h_a \times \cot \text{ (for Position "B"), i.e.}$$
$$K = 30 - 2(7.5) \times 1.732, \text{ or}$$
$$K = 30 - 25.98 = 4.02, \text{ and as the result}$$

$$\frac{4.02}{30} \times 100 = 13.4\% \quad \text{(as the value of "K" in the indicated "B" Position).}$$

Another filament piece was then positioned adjacent and parallel to the first installed filament on the tube surface, making a spacing of about 1/16 in. (ca. 0.159 cm.) therebetween. As was the case with laying of the first filament, an extension of about 4¼ in. (ca. 10.8 cm.) was made with each of the ends of the filament beyond each of the respective ends of the tube on which it was put and which were free from actual physical securement thereupon.

This filament emplacement procedure was repeated a number of times until a total of 38 longitudinally-extending filaments had been secured on the tube.

After all 38 of the filaments were so-positioned in relatively-identical equispacing about the tube exterior, several more thin layers of natural rubber latex were then sequentially brushed thereover; with drying time allowed between each of the additionally applied coatings. Several such extra coating layers were done.

Two (2) steel ½ in. diameter plain eyebolts of the common variety of such hardware were than taken for fitting preparation. Each of the eyebolts had threaded shanks that were about 3 in. (ca. 7.62 cm.) in length. A ½ in. hex nut was then screwed on the shank of each eyebolt to the spacing whereat there was about ½ in. clearance between the end of the eyebolt shank and the nearest side of mounted nut. Both of the hex nuts were then soldered in place to permanently join them with the shanks of the eyebolts on which they were provided. The peripheral edges of the integrated hex nuts were then ground smooth to facilitate better fitting within and more precise accommodation by the rubber tubing when pushed thereinto.

The central shank of one of the eyebolts was then drilled out from its bottom end centrally for a length of about 2½ in. (ca. 6.35 cm.) to provide a ¼ in. (ca. 0.635 cm.) passageway opening leading therethrough to the indicated depth. Another ¼ in. side bore was then made in the shank at about the 2½ in. spacing from the bottom end thereof at which said central opening terminated so as to make a continuous L-shaped opening in the eyebolt shank. A 2¼ in. (ca. 5.71 cm.) length of ¼ in. O.D. copper tubing was then inserted into the lateral bore hole in the shank so as to extend perpendicularly therefrom, wherein it was securely soldered into place Nominally-sized ¼ in. compression fittings were connected to the extending end of the copper tubing to facilitate the making of fluid-handling and -transmitting connections therewith.

The so-provided, fluid-handling eyebolt fitting connector was then inserted into one end of the filament-provided tube The depth of the insertion was about 2¼ in. The unbored eyebolt fitting was then inserted into the other end of the expandable conduit tube to about the same depth. The shoulder portion of each of the eyebolt fittings (constituted by the ground-off hex nut attachments) caused noticable swellings in each end of the ends of the filament-provided tube as the respective fittings were physically inserted into the open tube ends.

The same "DACRON" cordage as was utilized for the emplaced filaments was then used to tightly wrap each end of the tube after eyebolt insertion to very strongly secure the emplaced filaments upon the tube at each inserted eyebolt location. Each of the wrappings was so made starting just on the eyebolt (or extending) side of the fitting at about the point where tube diameter swelling was caused to commence due to insertion of the hex nut shoulder in each fitting. Each wrapping was done by winding the polyester line very closely away (centrally towards the middle of the tube) in a more-or-less single-layer binding with no between-turn spacing until about an inch (ca. 2.54 cm.) in length of the filament-encased tube had been so bound. The free ends of the wrapping lines were tightly secured to prevent their unloosenments. As an additional precaution against unwanted unbinding, the loose ends or the longitudinally-extending filaments were then folded back over the already-wrapped portion thereof. After this, about a ½ in. portion of the length of the folded-over area was yet further additionally tightly bound with further wrappings of the polyester cordage.

After the tube end safety wrappings were made, the free ends of the longitudinally-extending filaments emplaced along and bindingly-attached to the tube surface were each and individually tied into knots which were made as close as possible to the wrapped binding makeup. These knot clumpages further served to prevent any slippage of the longitudinally-extending filaments out from under the end-binding wrappings which helped their securement on the tube of the expandable conduit member so formed. Following all of this, a further coated layer of rubber latex was made about the wrapped areas to additionally prohibit knot and other unloosenings in the structures; this finishing step constituting the essential completion of the expandable conduit member, per se.

The so-fabricated expandable conduit member was then tested for performance capability in the device into which it had been formed. This was done by first securely hanging one end of the device to a ceiling through one of the integrated eyebolt fittings therein provided. After that, 400 lbs. of steel weights were suspended from the other, then-lowermost eyebolt fitting. A section of nominal ¼ in. polypropylene tubing equipped with valves and a pressure guage was then fitted and installed to couple the fluid connection on one of the eyebolt fittings made to be fluid-handling to a city water source having a tap pressure of about 80 psig. After this, the contractile device was inflated and deflated a number of times in order to pre-stretch the attached polyester filaments. The distance between the eyebolts in the end fittings on the tube was measured before and after each inflation.

The maximum filament-provided tubular conduit expansion found to be tolerable was, at its central portion, an O.D. measure of about 3 in. (ca. 7.62 cm.). With a maximum fluid pressure applied of about 24 psig, the maximum contraction stroke measured from eyebolt-to-eyebolt upon inflation of the expandable conduit at that pressure for getting the full 3 in. diametrically-measurable inflation of the filament-provided tube as about ¼ in. Despite the relatively short lift-stroke involved, the power capability of the device in being easily able to lift the 400 lb. load vertically-upwards was thus nicely and convincingly demonstrated.**
(** See ADDENDUM)

Second Illustration

The basic expandable conduit-fabricating procedure of the First Illustration was substantially repeated excepting to: use ohly a 5½ in. (13.97 cm.) length of the gum rubber tubing; employ 50 lb. test nylon monofilament fishing line for the longitudinally-extending filamentary material utilized; use tube end-closing fittings that were not mechanical couplings in and of themselves (although one of them was adapted to handle fluid to be injected within the tubing); and to allow the emplaced filaments to extend beyond the ends of the tube for fastening to the mechanical coupling means separate from the end-closing hardware that were utilized to inter-connect the device for support and load-moving purposes.

Each of the nylon filaments employed had a length of about a foot (ca. 30.5 cm.). Thirty-two (32) filaments were applied about the tube surface in about equispaced relative physical disposition so as to lay parallel to the center line of the tube and to extend for several inches past each of the tube ends. As in the First Illustration, rubber latex was utilized for affixing the nylon filaments on and circumferentially about the gum rubber tube surface.

A ½ in. long piece of ½ in. diameter steel rod was

** ADDENDUM

To demonstrate an additional practical application of the expandable conduit assembly described in the First Illustration hereof, the same device therein fabricated is installed in the handle portion of an ordinary pole-type tree pruning or trimming device of the sort that operates by pulling a cord to close the scissors-like cutter at the extended extremity of the appliance (this, as is well known, usually being done by hand). The trimmer, which has length of about 12 feet, is equipped with the contractile apparatus assembly of the First Illustration so that the pull cord is attached to the tractile-moving end of the expandable conduit member with the other end of the assembly firmly attached near the end of the handle part of the trimmer. The expandable conduit member is operated by water under city tap pressure (about 80 psig) by connection with an ordinary garden hose of nominal ½ in. size with a quick-opening valve included in the hose near its connection with the contractile device. Operation of the trimmer is nicely and neatly done for cutting purposes by simple opening of the valve to pressurize the expandable conduit member. Use of the contractile device with the trimmer actually makes it more convenient and accurate to accomplish the desired tree trimming, since the pole appliance is easier to handle and manipulate without requirement to use one hand for the pulling of the cord to operate the cutting mechanism when the appliance is set in the desired trimming position with appropriate and wanted location of the cutting element in the tree about the twig needing to be severed. covered with a cyanoacrylate adhesive composition and then inserted into one end of the nylon filament-covered tubeing wherein, within several seconds, the adhesive cured and held the plug tightly in end-closing place.

Another identical steel plug (i.e., ½ in. of ½ in. rod) was drilled along its cylindrical center line so as to have a 1/8 in. (0.0.3175 cm.) passageway hole therethrough. A piece of 1/8 in. O.D. copper tubing 4 in. (10.16 cm.) in length was forced into one end of the drilled-out plug and therein soldered in place to make a fluid-handling connecting duct therewith. This passageway-containing end plug was then cemented into the remaining open end of the tube with the cyanoacrylate adhesive.

After complete curing of the cyanoacrylate adhesive holding both the solid and open end plugs in the tube openings, both ends of the nylon filament-provided tube were tightly wrapped with ordinary black electrical tape up to a distance of about 1 in. in from each of the tube ends. A ½ in. wide screw-band type of hose clamp was then tightened around each end of the filament-wrapped tube, having first been positioned before locking thereof so as to be precisely over the steel plug end-closing inserts. The clamps served to further secure and fix the tube end closures in order to additionally ensure that there would be no pulling away of the tube from the plugs upon fluid-pressuring inflation of the tube.

The loose and unaffixed ends of the nylon filaments extending beyond the tube ends were, from each end of the tube, respectively passed through a 5/16 in. (ca. 0.794 cm.) diameter hole drilled in the center of separate 1/16 in. (ca. 0.159 cm.) thick steel plate brackets having flat dimensions of ½×1½ in. The respective arrays of nylon filaments extending from each tube end and passed through each central opening in each of the respective plate brackets were thermally severed with a propane torch at a distance of about 2 in. beyond the plate bracket openings. The filament-cutting, thermo-severing operation left a large formation of fused nylon at the ends of the filaments in each of the arrays extending from the respective sealed tube terminations. The melted ends of the nylon filaments in each of the extending arrays were then bunched together and encased in a large glob of epoxy adhesive material which was used not only to bond the filaments together but to also tightly bond and secure them to the respective bracket plates through which they had been passed.

Two (2) additional 5/16 in. holes were then drilled in each of the bracket plates so as to be (in both of said plates) situate one on each side of the center hole through which the filaments had been passed. The bracket plates were then each identically fitted with respective U-bolts in order to provide mechanical coupling means for the device. The nylon filament array extending from the end of the tube having the fluid-connecting plug closure insert were parted slightly to make room for the 1/8 in. copper tubing extending from the plug. With this, the contractile device was essentially complete and ready for testing.

The so-fabricated contractile device was then tested by constructing a mechanical arm out of wood that was quite similar to the prosthetic appliance illustrated in FIG. 10 of the Drawing; excepting that, instead of having a forearm portion and a hand part, a wooden 2 in.×4 in. in cross-section (i.e., a "nominal" and ordinary 2×4 piece) extension from the elbow with a hook at its free end was utilized in the construction.

Pressure measuring (guage) means and valving were connected to the fluid port in the expandable conduit member so that tap water at 80 psig could be thereinto introduced for tubing inflation.

The mechanical arm was then tested under fluid-activating pressure from the water supply tap. As had been anticipated, when the contractile device linked up in the mechanical arm construction was activated by injection of water under pressure into the expandable conduit member of the device, the arm would rise about its elbow section and was capable of lifting various weights that had been suspended from the hook at the 2×4 end for test purposes. The operation of the prototype prosthetic appliance, rudimentary as it was for test purposes, was quite satisfactory and utilitarian.

Third Illustration

There was fabricated in pursuance with the present invention an expandable conduit member of the segmentally-constrictively-bounded or -cinched type of the style illustrated in FIG. 8 of the Drawing. This was done by following some of the ways explained for making of such constructions of both the First and the Second above-given Illustrations.

For the fabrication, the same size gum rubber tubing was utilized excepting to employ a 27.5 in. (69.85 cm.) length thereof. The longitudinally-extending filamentary material used was a 170 lb. test twisted nylon twine cordage. Each filament length employed was several inches longer than the length of the tube.

Following the filament-emplacement procedure of the Second Illustration, 32 lengths of the cut nylon twine pieces were in about equispaced relationship mounted about the tube so as to be parallel to its center line with the free, unattached ends of the filaments extending beyond each end of the tube.

The filament-covered tube was then girded or banded at about equally-spaced intervals along the tube length. This was accomplished by making several tightly-wound, circumferentially-laid wrappings of the nylon twine about the tube at the intervals at which it was desired to make each constrictive binding. The first site, or starting winding, of these was made at a position about 4.75 in. (ca. 12.07 cm.) in from one end of the filament-covered tube. After that, four (4) more identical wrappings were made along the length of the tube towards its other end with about 4.5 in. (ca. 11.43 cm.) spacings therebetween, including the spacing of that from the first winding made. The ends of the nylon twine in each of the circumferentially-wrapped bindings were securely fastened; and each of the wrappings were coated with several layers of independently dried rubber latex applications. The procedure resulted in the filament covered tube having six (6) distinct and individually-balloonable segments therein, each of which were capable of expansion upon fluid-pressuring inflation of the entire expandable conduit member.

The same type of end plugs (one of which was drilled and outfitted with a copper tube port) as employed in the Second Illustration were utilized and cyanoacrylate-cemented to make the end closures for the filament-covered, segmented tube; the only difference being that the plugs were each 1 in. lengths of the ½ in. diameter steel rod. Likewise, repeating what was done in the Second Illustration, the tube ends were wrapped with electrical tape then additionaly tightened with the same sort of hose clamps about the end-inserted plug closures.

At one end of the segmented tube, the loose ends of the extending nylon twine were inserted through a 5/16 in. diameter hole bored in the same style of bracket plate as prepared and utilized in the Second Illustration. The bracket plate was likewise outfitted with a U-bolt; and the loose ends of the twine array that had been inserted through the central hole in the bracket plate were melted off at a distance of about 2¼ in. (5.715 cm.) from the tube end wherefrom they extended then coated with a large glob of epoxy adhesive to constrain them in place and prevent back-slipping through the central hole in the bracket plate.

At the opposite end of the tube, the extending ends of the array of nylon twine filamentary material were secured to a different sort of mechanical intercoupling unit. This coupler was made from a 2.75 in. (6.985 cm.) length of ½ in. diameter threaded steel rod. A ½ in. hex nut was then screwed onto the rod until its outer end was flush with the end of the rod section. A ½ in. I.D./1-¼in. O.D. steel washer was then placed over the free end of the rod and moved therealong until it was adjacent to the mounted hex nut. After that, six (6) ½ in. I.D./1 in. O.D. steel washers were also placed over the rod and stacked adjacent to the first larger washer next to the hex nut. Then, another ½ in. hex nut was screwed onto the free end of the threaded rod and tightened down against the 1 in. washers placement.

The loose ends of the nylon filamentary material were then positioned uniformly around the stack of 1 in. washers such that the 1¼ in. end washer on the rod was nearest of the washers to the tube end from which the twine ends extended and the rod itself was disposed parallel with the longitudinal direction of the filament-covered tube. The loose ends of the twine were then tightly wrapped about the 1 in. washer stack with several turns of the same grade of nylon twine, following which the remaining free ends of the nylon twine array were folded back over the already-wrapped portion thereof with the area being then re-wrapped with more of the nylon twine. After securing the wrapping twine ends, the remaining loose ends of the filamentary material in the array emanating from the tube end were knotted as close as possible to the wrapping. All of the nylon twine ends were then permanently affixed and secured to the washers in the coupling unit by coating them with a thick layer of a strong polyurethane adhesive.

Even though the above-fabricated contractile device had a significantly greater length than that of the First Illustration, its contractability in unconstricted, non-segmented form would not be expected to be remarkably different from that of the device as made in the First Illustration. This is because of the indicated fact that the particular size of gum rubber tubing involved is safely capable of being expanded to a maximum diameter of approximately 3 in.; the same limiting to a material degree the expectable contraction stroke distance achievable upon ballooning of the tube by means of internal fluid activation.

When the above-fabricated, segmented expandable conduit member was inflated with water at about 24 psig, it contracted to a total of about 1 in. By comparison, the contraction of a non-segmented version of the same was only about ¼ in. under the same fluid-actuating water pressurization. In this connection, the contractability of each of the constricted segments in the segmented expandable conduit member acts and functions quite similarly to a separate conduit portion (with contractability expectations being calculable for each individual segment of the Structure following the determinations for any given individual expandable conduit member as done per the foregoing Contractability Demonstration).

Analogous excellent results are obtained when other robotic, fluid-actuated muscle analogue devices are made and used from other materials of construction with the same or varying techniques of fabrication as compared to those involved in the foregoing Illustrations in keeping of practice of the invention.

It is to be recognized that many modifications can be readily made in following of the present invention without substantial departation from its apparent and intended spirit and scope as to embodimentation and practice thereof, which is all pursuant to and in accordance with that which is set forth and delineated in the hereto-appended claims.

What is claimed is:

1. A robotic, fluid-actuated muscle analogue device adapted to exert contractile and pulling motive power upon its activation, which device is comprised of:
  a hollow expandable central conduit member containing an interior void space and having a expandable balloonable, fluid-confining wall structure thereabout and respective end portions terminating same, said expandable conduit member being characterizable in exhibiting end-to-end contractibility when inflated from a position of undistended upon admission thereinto within said interior void space thereof of a fluid under pressure for expanding activation of said conduit member;
  at least a single, longitudinally-extending strand of filamentary material running at least relatively peripherally as to, and fixedly secured with, said wall structure of the expandable conduit member of which said filamentary material is an integral part in physical attachment thereto, said filamentary material aligned so as to extend along from one end of the expandable conduit to another end of said conduit member in emplacement therewith that is at least substantially parallel with a longitudinal center line of said conduit, said filamentary material being further characterizable in having a tensile extensibility not in excess of the elongatability under internal fluid-pressurization of said expandable conduit member;

means connected into and with the void space in said hollow expandable conduit member for introducing fluid under pressure thereinto for inflationary activation thereof, whereby said expandable conduit member becomes so as to contractibly assume a foreshortened end-to-end length with corresponding lessening of the effective longitudinal span of the therewith emplaced and associated filamentary material; and mechanical means for interlinkingly coupling through and with extremity portions of said filamentary material the contractible ends of said expandable conduit member for physically anchoring same at and from one end thereof and connecting same to and with a load to be moved at and from the other end thereof, respectively.

2. A device in accordance with the device of claim 1, wherein
there is a plurality of said strands of longitudinally extending filamentary material emplaced with said expandable conduit member therewith integrally associated.

3. A device that is in accordance with that of claim 2 and including,
in addition thereto and further combination therewith
means connected out of and with the void space in said hollow expandable conduit member for exhausting fluid under pressure therefrom for deflationary venting deactivation thereof, whereby said expandable conduit member becomes depressurized and uninflated so as to be capable of return to its non-fluid-activated position of rest wherein it at least substantially assumes its original unballooned end-to-end length.

4. A device in accordance with the device of claim 2, wherein
at least part of said mechanical coupling means is adapted with passageway openings integrally thereinto built to simultaneously handle fluid under pressure for admission into or venting from, or both, said hollow void space in said expandable conduit member.

5. A device in accordance with the device of claim 2, wherein
all of said mechanical coupling means are adapted with passageway openings integrally thereinto built to simultaneously handle fluid under pressure for admission into and venting from said hollow void space in said expandable conduit member.

6. A device in accordance with the device of claim 2, wherein
said expandable conduit member is made of an elastomeric material and further is so fabricated as to have:
a body portion constituted by said wall structure thereof; with
openings at each respective end of said body portion which enter into said hollow void space of the expandable conduit member which is defined by said fluid-confining wall structure thereof.

7. A device in accordance with that of claim 6, wherein
the elastomeric material of construction of which said expandable conduit member is made is a synthetic polymeric elastomer.

8. A device in accordance with that of claim 6, wherein
the elastomeric material of construction of which said expandable conduit member is made is natural gum rubber.

9. A tubular body portion in a device that is in accordance with any one of the devices of claims 6-8.

10. An out-of-round, curvilinearly-cross-sectioned body portion in a device that is in accordance with any one of the devices of claims 6-8.

11. A polygonally-cross-sectioned body portion in a device that is in accordance with any one of the devices of claims 6-8.

12. A device in accordance with the device of claim 2, wherein
said plurality of strands of longitudinally-extending filamentary material is emplaced with at least about substantially uniform lateral equispacing between each of the peripherally-laid strands in physical attachment with said integrally-associated expandable conduit member.

13. A device in accordance with the device of claim 2, wherein
said plurality of strands of longitudinally-extending filamentary material is emplaced in a single encompassing layer array in physical attachment with said integrally-associated expandable conduit member and about said hollow interior void space therein.

14. A device in accordance with the device of claim 2, wherein
said plurality of strands of longitudinally-extending filamentary material (b) is emplaced in a plurality of superimposed layer arrays in physical attachment with said integrally associated expandable conduit member and about said hollow interior void space therein.

15. A device that is in accordance with any one of the devices of claims 12-14, inclusive, wherein
said plurality of longitudinally-extending filamentary material strands is laid upon and adhesively and cohesively attached to the outer wall surface of said expandable conduit member.

16. A device in accordance with that of claim 15, and including,
in addition thereto and further combination therewith
an applied layer coating of a resilient adhesive material deposited and affixed to said exterior wall surface of the expandable conduit member, within which
said plurality of longitudinally-extending filamentary material strands is physically embedded and cohesively contained.

17. A deposit of dried, natural gum rubber latex as the applied layer coating in a device according to that of claim 16.

18. A device that is in accordance with any one of the devices of claims 12-14, inclusive, wherein said plurality of longitudinally-extending filamentary strands is laid and mechanically-affixed within a corresponding plurality of longitudinally-extending, accommodating groove channels formed longitudinally in the outer wall surface of said expandable conduit member, with each of said strands of filamentary material being physically disposed and contained within one of said accommodating groove channels.

19. A device in accordance with that of claim 18, and including, in addition thereto and further combination therewith, an applied layer coating of a resilient adhesive material deposited over and affixed to said exterior wall surface of the expandable conduit member, underneath and at the lower portion of which said plurality of channel groove-contained, mechanically-affixed, longitudinally-extending filamentary strands is covered and further cohesively contained.

20. A deposit of dried, natural gum rubber latex as the applied layer coating in a device according to that of claim 19.

21. A device that is in accordance with any one of the devices of claims 12-14, inclusive, wherein said plurality of longitudinally-extending filamentary strands is laid is laid and mechanically-affixed and contained physically within the wall structure, per se, of said expandable conduit member with which said strands are in integral association and attachment.

22. A device that is in accordance with any one of the devices of claims 1, 2, 6-8 and 12-14, inclusive, wherein said filamentary material is of natural origin.

23. A device that is in accordance with any one of the devices of claims 1, 2, 6-8 and 12-14, inclusive, wherein said filamentary material is an organic fibrous material of natural origin that is selected from the Group consisting of natural proteinaceous fibrous materials, natural cellulosic fibrous materials and other natural high polymer substance fibrous materials.

24. A device that is in accordance with any one of the devices of claims 1, 2, 6-8 and 12-14, inclusive, wherein said filamentary material is an organic fiber-forming and fibrous material of synthetic origin.

25. A polyester as the said filamentary material in a device in accordance with that of claim 24.

26. A nylon as the said filamentary material in a device in accordance with that of claim 24.

27. A polyolefin as the said filamentary material in a device in accordance with that of claim 24.

28. A polyvinyl derivative material including copolymers of vinyl chloride and vinyl acetate as the said filamentary material in a device in accordance with that of claim 24.

29. A polyaramid material as the said filamentary material in a device in accordance with that of claim 24.

30. A device that is in accordance with any one of the devices of claims 1, 2, 6-8 and 12-14, inclusive, wherein said filamentary material is an inorganic fiber or filamentary strand of synthetic origin.

31. Strandular material of an inorganic fiber-forming substance that is selected from the Group consisting of carbon, graphite, boron and its fiber-forming derivatives, quartz, glass, aluminum silicates and non-ferrous metallic compositions as the said filamentary material in a device in accordance with that of claim 30.

32. Strandular material of a ferrous composition as the said filamentary material in a device in accordance with that of claim 30.

33. Steel as the filamentary material in claim 32.

34. A device in accordance with the device of claim 6, wherein at least one of said mechanical coupling means is adapted with passageway openings integrally thereinto built to simultaneously handle fluid under pressure for admission into or venting from, or both, said hollow void space in said expandable conduit member, with each of said mechanical coupling means being mounted and mechanically secured in the respective openings at each end of said body portion of said expandable conduit member.

35. The device of claim 34, wherein both of said mechanical coupling means are adapted with passageway openings integrally thereinto built to simultaneously handle fluid under pressure for admission into and venting from said hollow void space in said expandable conduit member.

36. A device in accordance with either one of those of claims 34 or 35, wherein said mechanical coupling means each have hooking portions therein formed which extend outwardly from the said contractible ends of said expandable conduit member.

37. A device in accordance with the device of claim 2, wherein said plurality of strands of longitudinally-extending filamentary material extends with freely-unattached loose extremity end portions thereof reaching beyond at least one of the longitudinal ends of the expandable conduit member, with said loose extremity end portions of the filamentary material being securely fastened to a mechanical means to make and provide an interlinking coupling arrangement from one of the contractible ends of said expandable conduit member to which the remainder of said filamentary material is securely affixed.

38. A device in accordance with the device of claim 2, wherein said plurality of strands of longitudinally-extending filamentary material extends with freely-unattached loose extremity end portions thereof reaching respectively beyond both of the longitudinal ends of the expandable conduit member, with each of said loose extremity end portions of the filamentary material being securely fastened to respective individual mechanical means to make and provide an inter-linking coupling arrangement from both of the respective contractible ends of said expandable conduit member to which the central remainder of said filamentary material is securely affixed.

39. A device in accordance with the device of claim 6, wherein at least one of said openings at one of the ends of said body portion of said expandable conduit member is sealingly-fitted with a mechanical end closure which is mechanically secured to the conduit member in order to cover said opening, and also wherein said plurality of strands of longitudinally-extending filamentary material extends with freely-unattached loose extremity end portions thereof reaching beyond at least one of the longitudinal ends of the expandable conduit member, with said loose extremity end portions of the filamentary material being securely fastened to a mechanical means to make and provide an interlinking coupling arrangement from one of the contractible ends of said expandable conduit member to which the remainder of said filamentary material is securely affixed.

40. The device of claim 39, wherein said mechanical end closure is an insertable plug form of fitting for closing and sealing the opening of said expandable conduit member in which it is mounted.

41. A device in accordance with the device of claim 40, wherein said mechanical end closure is provided with a central passageway therein for fluid-handling and -transmitting communication with said hollow void space in the expandable conduit member.

42. A device in accordance with the device of claim 6, wherein both of said openings at each of the respective ends of said body portion of said expandable conduit member are sealingly-fitted with respective mechanical end closures which are each mechanically secured to the conduit member in order to cover each respective opening thereof and also wherein said plurality of strands of longitudinally-extending filamentary material extends with freely-unattached loose extremity end portions thereof reaching respectively beyond both of the longitudinal ends of the expandable conduit member, with each of said loose extremity end portions of the filamentary material being securely fastened to respective individual mechanical means to make and provide an inter-linking coupling arrangement from both of the respective contractible ends of said expandable conduit member to which the central remainder of said filamentary material is securely affixed.

43. The device of claim 42, wherein both of said mechanical end closures are of an insertable plug form of fitting for closing and sealing respectively both of said openings of said expandable conduit member in which they are mounted.

44. A device in accordance with the device of claim 43, wherein at least one of said mechanical end closures is provided with a central passageway therein for fluid-handling and -transmitting communication with said hollow void space in the expandable conduit member.

45. A device that is in accordance with any one of the devices of claims 1–8, 12–14, 34, 35 and 37–44, inclusive, wherein there is included, in addition thereto and in further combination therewith, means associated with said expandable conduit member and/or mechanical attachments therewith for guiding the longitudinal movement thereof in its stroke pattern during its contraction upon fluid-actuating inflation and extension from a ballooned condition of inflation upon release of any fluid-actuating pressurization thereof.

46. A device that is in accordance with any one of the devices of claims 1–8, 12–14, 34, 35 and 37–44, inclusive, wherein there is included, in addition thereto and in further combination therewith, at least one engirdling, circumvelopingly-binding and -constricting cinch means along the length of said expandable conduit member for constraining and preventing inflationary expansion and distension of said conduit member at the site of the restraining cinch girdle thereof, whereby upon fluid-actuating pressurization of said expandable conduit member it is inflated in a series of sequentially segmented ballooned portions magnifying contractibility thereof.

47. A plurality of said cinch means constraining said expandable conduit member in a device that is in accordance with that of claim 46.

48. The device of claim 47, wherein said plurality of said cinch means are provided at about equispaced location sites along the length from end-to-end of said expandable conduit member.

49. A device according to that of claim 15 and including, in addition thereto and further combination therewith, at least one engirdling, circumvelopingly-binding and -constricting cinch means along the length of said expandable conduit member for constraining and preventing inflationary expansion and distension of said conduit member at the site of the restraining cinch girdle thereof, whereby upon fluid-actuating pressurization of said expandable conduit member it is inflated in a series of sequentially segmented ballooned portions magnifying contractibility thereof, 50. A device according to that of claim 18 and including, in addition thereto and further combination therewith, at least one engirdling, circumvelopingly-binding and -constricting cinch means along the length of said expandable conduit member for constraining and preventing inflationary expansion and distension of said conduit member at the site of the restraining cinch girdle thereof, whereby upon fluid-actuating pressurization of said expandable conduit member it is inflated in a series of sequentially segmented ballooned portions magnifying contractibility thereof.

51. A device according to that of claim 19 and including, in addition thereto and further combination therewith, at least one engirdling, circumvelopingly-binding and-constricting cinch means along the length of said expandable conduit member for constraining and preventing inflationary expansion and distension of said conduit member at the site of the resulting cinch girdle thereof, whereby upon fluid-actuating pressurization of said expandable conduit member it is inflated in a series of sequentially segmented ballooned portions magnifying contractibility thereof.

52. A device according to that of claim 21 and including, in addition thereto and further combination therewith, at least one engirdling, circumvelopingly-binding and-constricting cinch means along the length of said expandable conduit member for constraining and preventing inflationary expansion and distension of said conduit member at the site of the resulting cinch girdle thereof, whereby upon fluid-actuating pressurization of said expandable conduit member it is inflated in a series of sequentially segmented ballooned portions magnifying contractibility thereof.

53. A device according to that of claim 22, and including, in addition thereto and further combination therewith, at least one engirdling, circumenvelopingly-binding and -constricting cinch means along the length of said expandable conduit member for constraining and preventing inflationary expansion and distension of said conduit member at the site of the resulting cinch girdle thereof, whereby upon fluid-actuating pressurization of said expandable conduit member it is inflated in a series of sequentially segmented ballooned portions magnifying contractibility thereof.

54. A device according to that of claim 24 and including, in addition thereto and further combination therewith, at least one engirdling, circumenvelopingly-binding and -constricting cinch means along the length of said expandable conduit member for constraining and preventing inflationary expansion and distension of said conduit member at the site of the resulting cinch girdle thereof, whereby upon fluid-actuating pressurization of said expandable conduit member it is inflated in a series of sequentially segmented ballooned portions magnifying contractibility thereof.

55. A plurality of said cinch means constraining said expandable conduit member in a device that is in accordance with any one of the devices of claims 49-54, inclusive.

56. A device in accordance with the device of claim 55, wherein said plurality of said cinch means are provided at about equispaced location sites along the length end-to-end of said expandable conduit member.

57. A prosthetic appliance that is energized and powered for movement by and with an incorporated robotic, fluid-actuated muscle analogue device which is an embodiment of any one of the devices that are in accordance with those of claims 1-8, 12-14, 34, 35 and 37-44, inclusive.

58. A prosthetic appliance that is energized and powered for movement by and with an incorporated robotic, fluid-actuated muscle analogue device which is an embodiment of one that is in accordance with claim 46.

59. A prosthetic appliance that is energized and powered for movement by and with an incorporated robotic, fluid-actuated muscle analogue device which is an embodiment of one that is in accordance with either one of those of claims 47 or 48.

60. A prosthetic appliance that is energized and powered for movement by and with an incorporated robotic, fluid-actuated muscle analogue device which is an embodiment of one that is in accordance with claim 49.

61. A prosthetic appliance that is energized and powered for movement by and with an incorporated robotic, fluid-actuated muscle analogue device which is an embodiment of one that is in accordance with claim 50.

62. A prosthetic appliance that is energized and powered for movement by and with an incorporated robotic, fluid-actuated muscle analogue device which is an embodiment of one that is in accordance with claim 51.

63. A prosthetic appliance that is energized and powered for movement by and with an incorporated robotic, fluid-actuated muscle analogue device which is an embodiment of one that is in accordance with claim 52.

64. A prosthetic appliance that is energized and powered for movement by and with an incorporated robotic, fluid-actuated muscle analogue device which is an embodiment of one that is in accordance with claim 53.

65. A prosthetic appliance that is energized and powered for movement by and with an incorporated robotic fluid-actuated muscle analogue device which is an embodiment of one that is in accordance with claim 54.

66. A prosthetic appliance that is energized and powered for movement by and with an incorporated robotic, fluid-actuated muscle analogue device which is an embodiment of one that is in accordance with claim 55.

67. An animatable, robotically-operable construction assembly contrivance that is energized and powered for movement by and with an incorporated robotic, fluid-actuated muscle analogue device which is an embodiment of any one of the devices that are in accordance with those of claims 1-8, 12-14, 34, 35 and 37-44, inclusive.

68. An animatable, robotically-operable construction assembly contrivance that is energized and powered for movement by and with an incorporated robotic, fluid-actuated muscle analogue device which is an embodiment of on that is in accordance with claim 46.

69. An animatable, robotically-operable construction assembly contrivance that is energized and powered for movement by and with an incorporated robotic, fluid-actuated muscle analogue device which is an embodiment of one that is in accordance with either one of those of claims 47 or 48.

70. An animatable, robotically-operable construction assembly contrivance that is energized and powered for movement by and with an incorporated robotic, fluid-actuated muscle analogue device which is an embodiment of one that is in accordance with claim 49.

71. An animatable, robotically-operable construction assembly contrivance that is energized and powered for movement by and with an incorporated robotic, fluid-actuated muscle analogue device which is an embodiment of one that is in accordance with claim 50.

72. An animatable, robotically-operable construction assembly contrivance that is energized and powered for movement by and with an incorporated robotic, fluid-actuated muscle analogue device which is an embodiment of one that is in accordance with claim 51.

73. An animatable, robotically-operatable construction assembly contrivance that is energized and powered for movement by and with an incorporated robotic, fluid-actuated muscle analogue device which is an embodiment of one that is in accordance with claim 52.

74. An animatable, robotically-operatable construction assembly contrivance that is energized and powered for movement by and with an incorporated robotic, fluid-actuated muscle analogue device which is an embodiment of one that is in accordance with claim 53.

75. An animatable, robotically-operatable construction assembly contrivance that is energized and powered for movement by and with an incorporated robotic, fluid-actuated muscle analogue device which is an embodiment of one that is in accordance with claim 54.

76. An animatable, robotically-operatable construction assembly contrivance that is energized and powered for movement by and with an incorporated robotic, fluid-actuated muscle analogue device which is an embodiment of one that is in accordance with claim 55.

* * * * *

UNITED STATES PATENT AND TRADEMARK OFFICE
CERTIFICATE OF CORRECTION

PATENT NO. : 5,021,064
DATED : June 4, 1991
INVENTOR(S) : R. Scott Caines

It is certified that error appears in the above-identified patent and that said Letters Patent is hereby corrected as shown below:

Col 40 lines 56-57, after "a" delete "expandable."
Col. 40, line 58, delete "thereabout" and insert --about--, and
    before "and respective" insert -- said void space --.
Col 40 lines 59-60, delete "being characterizable in."
Col 41 lines 8-9, delete "being further characterizable in."
Col. 41, line 10, delete "the elongability" and insert
    -- a contraction of said filamentary material --.
Col 41 line 12, after "connected" delete "into and."
Col 41 line 16, after "becomes" insert -- ballooned --.
Col 41 line 25, between "and" and "connecting" insert -- respectively --.
Col 41 line 26, after "same at" delete "and from."
Col 41 line 27, after "same" delete "to and" and
    after "moved" delete "and from" and
    delete both the comma and the word "respectively" after "thereof."
Col 42 line 43, delete "(b)" entirely.

Signed and Sealed this

Fourteenth Day of September, 1993

Attest:

BRUCE LEHMAN

Attesting Officer      Commissioner of Patents and Trademarks